US008685967B2

(12) United States Patent
Ho et al.

(10) Patent No.: US 8,685,967 B2
(45) Date of Patent: Apr. 1, 2014

(54) SUBSTITUTED TRIAZOLOPYRIDINES AND ANALOGS THEREOF

(75) Inventors: Ginny D. Ho, Murray Hill, NJ (US); Elizabeth M. Smith, Verona, NJ (US); Eugenia Y. Kiselgof, Flemington, NJ (US); Kallol Basu, Piscataway, NJ (US); Zheng Tan, Edison, NJ (US); Brian McKittrick, New Vernon, NJ (US); Deen Tulshian, Lebanon, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 238 days.

(21) Appl. No.: 13/262,990

(22) PCT Filed: Apr. 5, 2010

(86) PCT No.: PCT/US2010/029908
§ 371 (c)(1),
(2), (4) Date: Oct. 5, 2011

(87) PCT Pub. No.: WO2010/117926
PCT Pub. Date: Oct. 14, 2010

(65) Prior Publication Data
US 2012/0028975 A1 Feb. 2, 2012

Related U.S. Application Data

(60) Provisional application No. 61/167,310, filed on Apr. 7, 2009.

(51) Int. Cl.
*A61K 31/437* (2006.01)
*A61K 31/5377* (2006.01)
*A61P 25/18* (2006.01)
*A61P 3/00* (2006.01)
*A61P 25/28* (2006.01)
*A61P 25/24* (2006.01)
*A61P 3/04* (2006.01)
*A61P 3/10* (2006.01)
*C07D 471/04* (2006.01)
*A61P 25/00* (2006.01)

(52) U.S. Cl.
USPC ......... 514/233.2; 514/303; 546/120; 544/127

(58) Field of Classification Search
USPC ................ 546/120; 514/303, 233.2; 544/127
See application file for complete search history.

(56) References Cited

U.S. PATENT DOCUMENTS

| 6,303,625 B1 * | 10/2001 | Hoekstra et al. ............ 514/303 |
| 2005/0020639 A1 | 1/2005 | Smith et al. |
| 2005/0229333 A1 | 10/2005 | Glenn et al. |
| 2006/0287324 A1 | 12/2006 | Sun et al. |
| 2010/0016303 A1 | 1/2010 | Ritzen et al. |

FOREIGN PATENT DOCUMENTS

| EP | 1277754 | 4/2001 |
| EP | 2168959 | 3/2010 |
| WO | WO2006135795 | 12/2006 |
| WO | WO2007113226 | 10/2007 |
| WO | WO2008/125111 | 10/2008 |
| WO | WO2008156094 | 12/2008 |
| WO | 2009146358 | * 12/2009 |
| WO | WO2009146358 | 12/2009 |

OTHER PUBLICATIONS

Torremans et al., Acta Neurobiol Exp (2010), vol. 70, pp. 13-19.*
Lawson et al., Bioorganic & Medicinal Chemistry Letters (2001), 11(19), 2619-2622.*
J. Kehler et al., "The Potential Therapeutic Use of Phosphodiesterase 10 Inhibitors", Expert Opinion, 2007, vol. 17, pp. 147-158, Informal Heathcare, UK.
M. Caira et al., Preparation and Crystal Characterization of a Polymorph,a Monohydrate, and an Ethyl Acetate Solvate of the Antifungal Fluconazole, J. Pharmaceutical Sci, 2004, vol. 93, pp. 601-611, Wiley-Liss, Inc. US.
E. C. van Tonder at el., "Preparation and Physicochemical Characterization of 5 Niclosamide Solvates and 1 Hemisolvate", AAPS PharmSciTech, 2004, vol. 5, Article 12, American Association of Pharmaceutical Scientists, American Association of Pharmaceutical Scientists, US.
A. L. Bingham et al,, "Over one Hundred Solvates of Sulfathiazole", Chem. Commun, 2001, pp. 603-604, published on http://pubs.rsc.org.
Remenar et al, "Crystal Engineering of Novel Cocrystals of a Triazole Drug with 1,4-Dicarboxylic Acids", J. Am. Chem. Soc, 2003, vol. 125, pp. 8456, American Chemical Society.
Berge et al., "Pharmaceutical Salts", J. of Pharmaceutical Sciences, 1977, vol. 66, pp. 1-19.
Gould, "Salt Selection for Basic Drugs", International J. of Pharmaceutics, 1986, vol. 22, pp. 201-217, Elsevier Science Publishers B.V.

* cited by examiner

*Primary Examiner* — Niloofar Rahmani
(74) *Attorney, Agent, or Firm* — John C. Todaro

(57) ABSTRACT

The present invention relates to substituted triazolopyridines and analogs thereof, the use of the compounds as phosphodiesterase 10 (PDE10) inhibitors for the treatment of PDE10-modulated disorders, to pharmaceutical compositions comprising the compounds.

5 Claims, No Drawings

SUBSTITUTED TRIAZOLOPYRIDINES AND ANALOGS THEREOF

CROSS REFERENCE TO RELATED APPLICATIONS

This application is the National Stage of International Application No. PCT/US2010/029909 filed on Apr. 5, 2010, which claims the benefit under 35 U.S.C. 119(e) of U.S. Provisional Application No. 61/167,310 filed Apr. 7, 2009.

FIELD OF THE INVENTION

The present invention relates to substituted triazolopyridines and analogs thereof, to the use of the compounds as phosphodiesterase 10 (PDE10) inhibitors for the treatment of PDE10-modulated disorders, and to pharmaceutical compositions comprising the compounds.

BACKGROUND OF THE INVENTION

PDE10 is known to be a dual cAMP/cGMP phosphodiesterase; see, for example, Kehler et al, "The potential therapeutic use of phosphodiesterase 10 inhibitors", *Expert Opin. Ther. Patents* (2007) 17(2):147-158.

PDE10 is expressed at high levels in all striatal medium spiny neurons (MSNs), but is expressed at much lower or undetectable levels elsewhere in the brain and periphery. By increasing cAMP and cGMP levels in all striatal MSNs, PDE10 inhibition will mimic D2 dopamine receptor antagonism in the indirect striatopallidal output pathway and will increase the activity of the direct striatonigral output pathway, thus more fully normalizing the reduced striatal output that characterizes schizophrenia. By increasing corticostriatal transmission, PDE10 inhibition should improve the cognitive dysfunction that characterizes schizophrenia. Furthermore, the discrete localization of PDE10 should lead to an improved side effect profile; typical side effects include extrapyramidal syndrome, diabetes, weight gain, hyperprolactinemia, sedation and $QT_c$ prolongation.

PDE10 inhibitors have also been reported to be useful in treating in other CNS (central nervous system) disorders such as psychosis, cognitive disorders (such as Alzheimer's disease), bipolar disorder, depression, diet-induced obesity, diabetes and metabolic syndrome.

Papaverine has been identified as a PDE10 inhibitor, and has been shown to be effective in animal models of schizophrenia.

8-Substituted triazolopyridine phosphodiesterase 4 inhibitors useful in the treatment of skin diseases are disclosed in WO 2008/125111. 6,7-Di-aryl/heteroaryl-substituted triazolopyridines are disclosed in US 2006/0287324. 6-Aminomethyl-substituted triazolopyridines and derivatives thereof are disclosed in WO 2007/113226. Imidazo- and triazolopyridine keratin dyeing compounds are disclosed in US 2005/0229333. Imidazo- and triazolopyridines useful in treating diseases associated with 11-beta-hydroxysteroid dehydrogenase type I are disclosed in WO 2006/135795. Imidazopyridines having phosphatidylinositol 3 kinase inhibitory activity are disclosed in EP 1277754.

SUMMARY OF THE INVENTION

In its several embodiments, the present invention provides a novel class of substituted triazolopyridine PDE10 inhibitor compounds and derivatives thereof represented by Formula I, below, pharmaceutical compositions comprising one or more of said compounds of Formula I, and methods of treating PDE10 inhibitor mediated disorders, for example CNS disorders such as schizophrenia, psychosis, cognitive disorders (such as Alzheimer's disease), bipolar disorder, depression, diet-induced obesity, diabetes and metabolic syndrome using said compounds of Formula I or pharmaceutical compositions comprising it.

Novel compounds of Formula I of the invention have the structural formula:

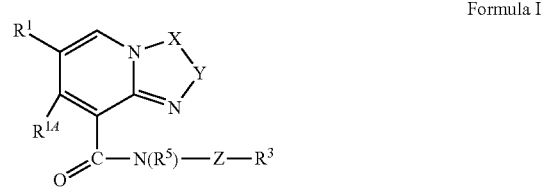

Formula I or a pharmaceutically acceptable salt thereof, wherein

—X—Y— is —N=C(R$^4$)—, —C(R$^4$)=N— or —C(R$^4$)=C(R$^4$)—;

R$^1$ is H, halo, alkyl, alkoxy, —CF$_3$, cycloalkyl, alkoxyalkoxy, OH, hydroxyalkyl, —OCF$_3$, —O-cycloalkyl, benzyloxy, —C(O)Oalkyl, —O-alkyl-CO$_2$H, —C(O)N(R$^6$)$_2$, —N(R$^6$)$_2$, -alkylN(R$^6$)$_2$, —NR$^6$—C(O)N(R$^6$)$_2$, —N(R$^6$)C(O)Oalkyl, —N(R$^6$)SO$_2$-alkyl, CN, —SF$_5$, —OSF$_5$, —SO$_2$R$^6$, —SR$^6$, trimethylsilylphenyl, aryl, —C≡C—CH$_2$OH, —C≡C-aryl, arylalkyl-, —C(O)NHCH$_2$-aryl, heteroaryl, —C≡C-heteroaryl, heteroarylalkyl-, —C(O)NHCH$_2$-heteroaryl,

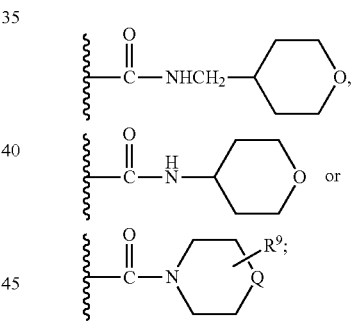

R$^{1A}$ is H, halo, alkyl, alkoxy, —CF$_3$, cycloalkyl, alkoxyalkoxy, OH, hydroxyalkyl, —OCF$_3$, —O-cycloalkyl, benzyloxy, —C(O)Oalkyl, —O-alkyl-CO$_2$H, —C(O)N(R$^6$)$_2$, —N(R$^6$)$_2$, -alkylN(R$^6$)$_2$, —NR$^6$—C(O)N(R$^6$)$_2$, —N(R$^6$)C(O)Oalkyl, —N(R$^6$)SO$_2$-alkyl, CN, —SF$_5$, —OSF$_5$, —SO$_2$R$^6$, —SR$^6$, trimethylsilylphenyl, —C≡C—CH$_2$OH, —C≡C-aryl, or arylalkyl-;

Q is —O—, —N(R$^{10}$)—, —S—, —SO—, —SO$_2$— or —CH$_2$—;

Z is:

—(CH(R$^2$))$_n$—(CH(R$^{2A}$))$_m$—,

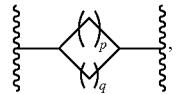

optionally substituted by 1 or 2 alkyl groups, or

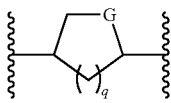

optionally substituted by 1 or 2 alkyl groups, wherein G is —N(R$^8$)—, —O— or —S—;

or —N(R$^5$)— and —Z— together form a 4 to 7 membered ring

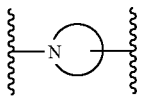

optionally substituted by 1 or 2 alkyl groups;

n is 1 or 2;

m is 0, 1 or 2;

p is 0, 1 or 2;

q is 0, 1, 2 or 3;

each R$^2$ is independently selected from the group consisting of H, alkyl or cycloalkyl;

each R$^{2A}$ is independently selected from the group consisting of H, alkyl, cycloalkyl, fluoro, OH, alkoxy, —N(R$^8$)$_2$ or -alkyl-N(R$^8$)$_2$;

R$^3$ is selected from the group consisting of pyridine, pyrazine,

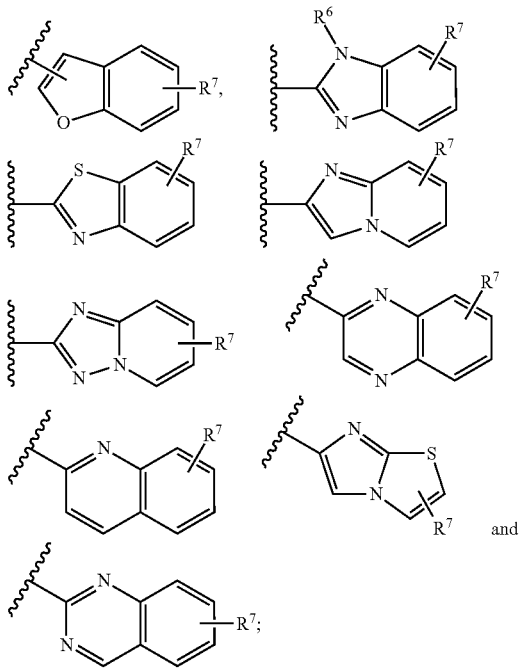

each R$^4$ is independently selected from the group consisting of H, alkyl, cycloalkyl, halo, —CF$_3$, alkoxyalkyl, heteroaryl, —CN, hydroxyalkyl, aryl, arylalkyl-, heteroarylalkyl-, —OCF$_3$, —SF$_5$, —OSF$_5$ and —N(R$^6$)$_2$;

R$^5$ is H, alkyl or cycloalkyl;

each R$^6$ is independently selected from the group consisting of H, alkyl, cycloalkyl and arylalkyl;

R$^7$ is 1 or 2 substituents independently selected from the group consisting of H, halo, alkyl, alkoxy, —CF$_3$, cycloalkyl, alkoxyalkoxy, OH, hydroxyalkyl, —OCF$_3$, —O-cycloalkyl, benzyloxy, —C(O)Oalkyl, —O-alkyl-CO$_2$H, —C(O)N(R$^6$)$_2$, —N(R$^6$)$_2$, -alkylN(R$^6$)$_2$, —NR$^6$—C(O)N(R$^6$)$_2$, —N(R$^6$)C(O)Oalkyl, —N(R$^6$)SO$_2$-alkyl, phenyl, CN, —SF$_5$, —OSF$_5$, —SO$_2$R$^6$, —SR$^6$ and trimethylsilyl;

each R$^8$ is independently selected from the group consisting of H and alkyl;

R$^9$ is 1 to 3 substituents independently selected from the group consisting of H and alkyl, and when Q is —CH$_2$—, R$^9$ can also be halo, OH, alkoxy or —CF$_3$; and R$^{10}$ is H, alkyl, —C(O)N(R$^6$)$_2$, —C(O)Oalkyl, or —SO$_2$-alkyl.

The present invention also relates to a pharmaceutical composition comprising at least one compound of Formula I or a pharmaceutically acceptable salt thereof in a pharmaceutically acceptable carrier.

In another embodiment, the present invention relates to a method of treating PDE10 mediated disorders, for example CNS disorders such as schizophrenia, psychosis, cognitive disorders (such as Alzheimer's disease), bipolar disorder, depression, diet-induced obesity, diabetes and metabolic syndrome comprising administering a therapeutically effective amount of at least one compound of Formula I or a pharmaceutically acceptable salt thereof to a mammal in need of such treatment. In another embodiment, the invention relates to a method of treating PDE10 mediated disorders, for example CNS disorders such as schizophrenia, psychosis, cognitive disorders (such as Alzheimer's disease), bipolar disorder, depression, diet-induced obesity, diabetes and metabolic syndrome comprising administering to a mammal in need of such treatment a pharmaceutical composition comprising a therapeutically effective amount of at least one compound of Formula I or a pharmaceutically acceptable salt thereof and a pharmaceutically acceptable carrier.

The invention also provides a novel class of PDE10 inhibitor compounds and derivatives thereof represented by Formula II, below, pharmaceutical compositions comprising one or more of said compounds of Formula II, and methods of treating PDE10 inhibitor mediated disorders, for example CNS disorders such as schizophrenia, psychosis, cognitive disorders (such as Alzheimer's disease), bipolar disorder, depression, diet-induced obesity, diabetes and metabolic syndrome using said compounds of Formula II or pharmaceutical compositions comprising it.

Novel compounds Formula II of the invention have the structural formula:

Formula II

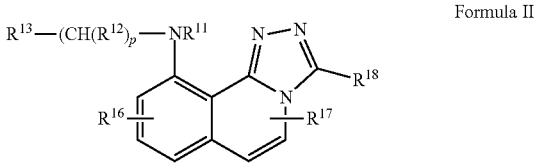

or a pharmaceutically acceptable salt thereof, wherein
p is 1, 2 or 3;
$R^{11}$ is H, alkyl or cycloalkyl;
$R^{12}$ is independently H, alkyl or cycloalkyl;
$R^{13}$ is selected from the group consisting of pyridine, pyrazine,

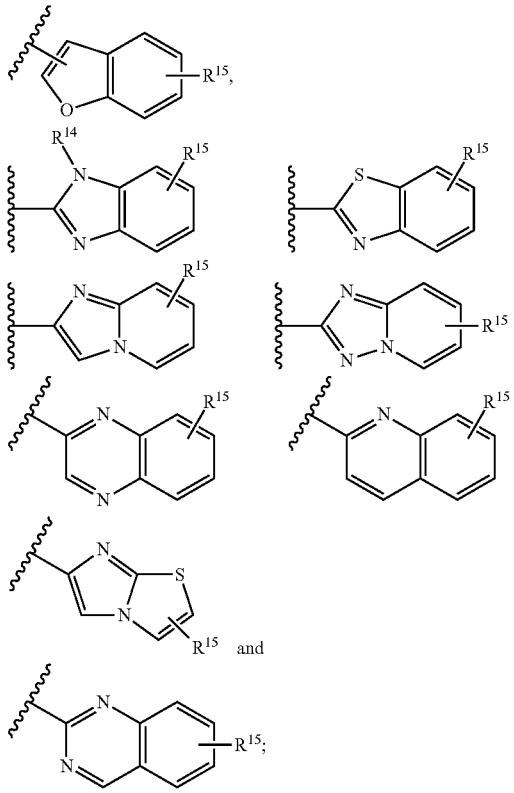

$R^{14}$ is H, alkyl, cycloalkyl or arylalkyl;
$R^{15}$ is 1 or 2 substituents independently selected from the group consisting of H, halo, alkyl, alkoxy, —$CF_3$, cycloalkyl, alkoxyalkoxy, OH, hydroxyalkyl, —$OCF_3$, —O-cycloalkyl, benzyloxy, —C(O)Oalkyl, —O-alkyl-$CO_2$H, —C(O)N($R^{14}$)$_2$, —N($R^{14}$)$_2$, -alkylN($R^{14}$)$_2$, —$NR^{14}$—C(O)N($R^{14}$)$_2$, —N($R^{14}$)C(O)Oalkyl, —N($R^{14}$)$SO_2$-alkyl, phenyl, CN, —$SF_5$, —$OSF_5$, —$SO_2R^{14}$, —$SR^{14}$ and trimethylsilyl;

$R^{16}$ 1, 2 or 3 substituents independently selected from the group consisting of H, halo, alkyl, alkoxy, —$CF_3$, cycloalkyl, alkoxyalkoxy, OH, hydroxyalkyl, —$OCF_3$, —O-cycloalkyl, benzyloxy, —C(O)Oalkyl, —O-alkyl-$CO_2$H, —C(O)N($R^{14}$)$_2$, —N($R^{14}$)$_2$, -alkylN($R^{14}$)$_2$, —$NR^{14}$—C(O)N($R^{14}$)$_2$, —N($R^{14}$)C(O)Oalkyl, —N($R^{14}$)$SO_2$-alkyl, phenyl, CN, —$SF_5$, —$OSF_5$, —$SO_2R^{14}$, —$SR^{14}$ and trimethylsilyl;

$R^{17}$ is 1 or 2 substituents independently selected from the group consisting of H, halo, alkyl, alkoxy, —$CF_3$, cycloalkyl, alkoxyalkoxy, OH, hydroxyalkyl, —$OCF_3$, —O-cycloalkyl, benzyloxy, —C(O)Oalkyl, —O-alkyl-$CO_2$H, —C(O)N($R^{14}$)$_2$, —N($R^{14}$)$_2$, -alkylN($R^{14}$)$_2$, —$NR^{14}$—C(O)N($R^{14}$)$_2$, —N($R^{14}$)C(O)Oalkyl, —N($R^{14}$)$SO_2$-alkyl, phenyl, CN, —$SF_5$, —$OSF_5$, —$SO_2R^{14}$, —$SR^{14}$ and trimethylsilyl; and $R^{18}$ is H, alkyl, cycloalkyl, halo, —$CF_3$, alkoxyalkyl, heteroaryl, —CN, hydroxyalkyl, aryl, arylalkyl-, heteroarylalkyl-, —$OCF_3$, —$SF_5$, —$OSF_5$ or —N($R^6$)$_2$;

The present invention also relates to a pharmaceutical composition comprising at least one compound of Formula II or a pharmaceutically acceptable salt thereof in a pharmaceutically acceptable carrier.

In another embodiment, the present invention relates to a method of treating PDE10 mediated disorders, for example CNS disorders such as schizophrenia, psychosis, cognitive disorders (such as Alzheimer's disease), bipolar disorder, depression, diet-induced obesity, diabetes and metabolic syndrome comprising administering a therapeutically effective amount of at least one compound of Formula II or a pharmaceutically acceptable salt thereof to a mammal in need of such treatment. In another embodiment, the invention relates to a method of treating PDE10 mediated disorders, for example CNS disorders such as schizophrenia, psychosis, cognitive disorders (such as Alzheimer's disease), bipolar disorder, depression, diet-induced obesity, diabetes and metabolic syndrome comprising administering to a mammal in need of such treatment a pharmaceutical composition comprising a therapeutically effective amount of at least one compound of Formula II or a pharmaceutically acceptable salt thereof and a pharmaceutically acceptable carrier.

DETAILED DESCRIPTION

In one embodiment of the invention, the compound has the structural Formula I.
In one embodiment of Formula I, —X—Y— is —C($R^4$)=N—.
In one embodiment of Formula I, —X—Y— is —N=C($R^4$)—.
In one embodiment of Formula I, —X—Y— is —C($R^4$)=C($R^4$)—.
In one embodiment of Formula I, Z is —(CH($R^2$))$_n$—(CH($R^{2A}$))$_m$—.
In one embodiment of Formula I, Z is —(CH($R^2$))$_n$—(CH($R^{2A}$))$_m$— and the sum of n and m is 1-3, preferably 2-3.
In one embodiment of Formula I, Z is —(CH($R^2$))$_n$—(CH($R^{2A}$))$_m$—; $R^2$ is H or alkyl, preferably H or methyl, more preferably H; and $R^{2A}$ is H or alkyl, preferably H or methyl, more preferably H.
In one embodiment of Formula I, Z is —(CH($R^2$))$_n$—(CH($R^{2A}$))$_m$—; the sum of n and m is 1-3, preferably 2-3; $R^2$ is H or alkyl, preferably H or methyl, more preferably H; and $R^{2A}$ is H or alkyl, preferably H or methyl, more preferably H.
In one embodiment of Formula I, $R^1$ is H, halo, heteroaryl, aryl or —C≡$CH_2$OH, wherein heteroaryl is pyridyl or thienyl and aryl is optionally substituted phenyl. Preferred optional substituents on phenyl are alkyl, halo, OH, alkoxy and —$CF_3$. Preferably, $R^1$ is H, F, Br, pyridyl, OH-phenyl or —C≡C—$CH_2$OH. More preferably, $R^1$ is H, F or Br.
In another embodiment of Formula I, $R^{1A}$ is H.
In another embodiment if Formula I, $R^3$ is selected from the group consisting of

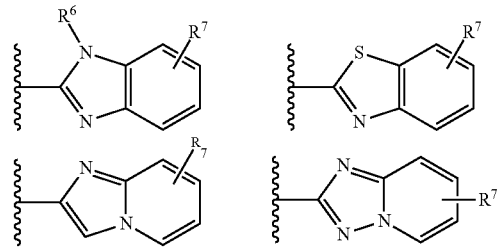

-continued

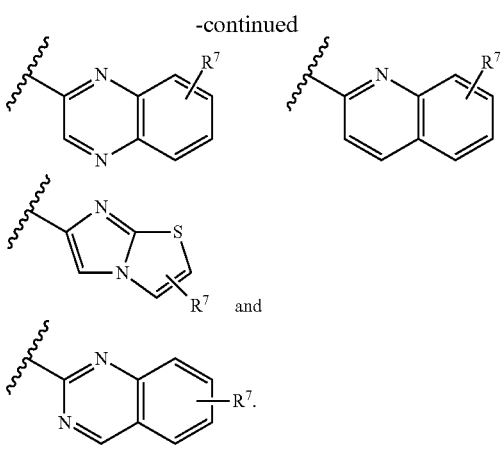

In another embodiment of Formula I, $R^3$ is

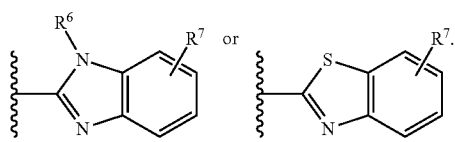

Preferably, $R^3$ is benzimidazolyl, optionally substituted in the benzene ring by 1 or 2 $R^7$ substituents independently selected from H, halo, alkyl and alkoxy groups and in the imidazo portion at $R^6$ by H or alkyl. Preferably, $R^7$ is one substituent selected from the group consisting of H, F, Br, Cl and —OCH$_3$, or $R^7$ is two substituents independently selected from Cl and F. $R^6$ is preferably H, methyl or ethyl, more preferably H.

In another embodiment of Formula I, $R^4$ is alkyl, cycloalkyl, halo, —CF$_3$ or alkoxyalkyl. Preferably, $R^4$ is methyl, ethyl, propyl, isopropyl, t-butyl, cyclopropyl, cyclobutyl, Br, —CF$_3$ or methoxyethyl. When $R^4$ is heteroaryl, it is preferably furanyl.

In another embodiment of Formula I, $R^5$ is H or alkyl. Preferably, $R^5$ is H or ethyl.

In another embodiment of the compounds of Formula I:
—X—Y— is —C(R$^4$)=N— or —N=C(R$^4$)—;
Z is —(CH(R$^2$))$_n$—(CH(R$^{2A}$))$_m$—;
the sum of n and m is 1-3, preferably 2-3;
$R^2$ is H or methyl;
$R^{2A}$ is H or methyl;
$R^1$ is H, halo, pyridyl, optionally substituted phenyl or —C≡C—CH$_2$OH;
$R^{1A}$ is H;
$R^3$ is

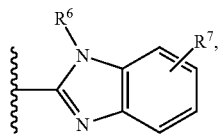

wherein $R^7$ is 1 or 2 substituents independently selected from H, halo, alkyl and alkoxy, and $R^6$ is H or alkyl;
$R^4$ is alkyl, cycloalkyl, halo, —CF$_3$ or alkoxyalkyl; and
$R^5$ is H or alkyl.

In another embodiment of Formula I,
—X—Y— is —C(R$^4$)=N— or —N=C(R$^4$)—;
Z is —(CH(R$^2$))$_n$—(CH(R$^{2A}$))$_m$—;
the sum of n and m is 1-3, preferably 2-3;
$R^2$ is H or methyl;
$R^{2A}$ is H or methyl;
$R^1$ is H, F, Br, pyridyl, OH-phenyl or —C≡C—CH$_2$OH;
$R^{1A}$ is H;
$R^3$ is

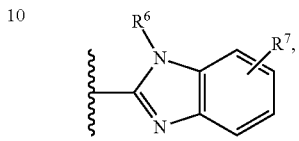

wherein $R^7$ is one substituent selected from the group consisting of H, F, Br, Cl and —OCH$_3$, or $R^7$ is two substituents independently selected from Cl and F, and wherein $R^6$ is H, methyl or ethyl;
$R^4$ is methyl, ethyl, propyl, isopropyl, t-butyl, cyclopropyl, cyclobutyl, Br, —CF$_3$ or methoxyethyl; and
$R^5$ is H or ethyl.

Preferred compounds of Formula I are those in Examples 1A, 1B, 1E, 1I, 1O, 1P, 1Q, 1R, 1S, 1T, 1AA, 1BB, 1DD, 1FF, 1GG, 1HH, 1II, 1LL, 1MM, 1NN, 1UU, 1XX, 1ZZ, 1BBB, 1DDD, 1FFF, 2B, 2D, 2F, 2G, 4A, 4D, 4E, 4F, 5B, 7A, 7D, 7E, 7K and 7O. More preferred compounds of Formula I are those in Examples 1GB, 1M, 1N, 1O, 1P, 1Q, 1Z, 1EE, 1SS, 1VV, 2B, 2F, 4D and 7O.

In another embodiment of the invention, the compounds have the structural Formula II.

In one embodiment of Formula II, p is 2 or 3.
In one embodiment of Formula II, $R^{11}$ is H or alkyl. Preferably, $R^{11}$ is H.
In another embodiment of Formula II, $R^{12}$ is H or alkyl. Preferably, $R^2$ is H or methyl, more preferably H.
In another embodiment if Formula II, $R^{13}$ is

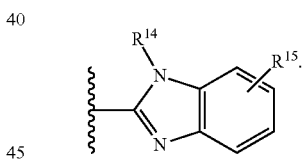

Preferably, $R^{15}$ is 1 or 2 substituents independently selected from H, halo, alkyl and alkoxy groups and $R^{14}$ is H or alkyl. Preferably, $R^{15}$ is H and $R^{14}$ is methyl.

In another embodiment of Formula II, $R^{16}$ and $R^{17}$ are each H.

In another embodiment of Formula II, $R^{18}$ is alkyl or —CF$_3$. More preferably, $R^{18}$ is t-butyl or —CF$_3$.

In another embodiment of Formula II,
p is 2 or 3;
$R^{11}$ is H or alkyl, preferably, H;
$R^{12}$ is H or alkyl, preferably, H or methyl; and
$R^{13}$ is

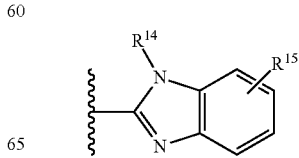

wherein $R^{15}$ is preferably 1 or 2 substituents independently selected from H, halo, alkyl and alkoxy groups, more preferably H, and $R^{14}$ is H or alkyl, more preferably methyl;

$R^{16}$ and $R^{17}$ are each H; and $R^{18}$ is alkyl or —$CF_3$, preferably, t-butyl or —$CF_3$;

Preferred compounds of Formula II are those in Example 8, 8B and 8C.

As used herein, the following terms are as defined below unless otherwise indicated:

Mammal means humans and other mammalian animals.

The following definitions apply regardless of whether a term is used by itself or in combination with other terms, unless otherwise indicated. Therefore, the definition of "alkyl" applies to "alkyl" as well as the "alkyl" portions of "hydroxyalkyl", "haloalkyl", "alkoxy", etc.

Alkyl means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain.

Hydroxyalkyl represents an alkyl group as defined substituted by 1 to 3 hydroxy groups. The bond to the parent is through the alkyl group.

Alkoxy means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

Halogen represents fluoro, chloro, bromo and iodo.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

"Cycloalkyl" means a non-aromatic mono- or multicyclic ring system comprising about 3 to about 10 carbon atoms, preferably about 3 to about 7 carbon atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Heteroarylalkyl" means a heteroaryl-alkyl- group in which the heteroaryl and alkyl are as previously described. Preferred heteroaralkyls contain a lower alkyl group. Non-limiting examples of suitable heteroaralkyl groups include pyridylmethyl, and quinolin-3-ylmethyl. The bond to the parent moiety is through the alkyl.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, —$CH(Y_1)(Y_2)$, —O—$Y_1$, hydroxyalkyl, alkoxyalkyl, alkoxyalkoxyalkyl, haloalkoxy, —$C(O)Y_1$, halo, nitro, cyano, —$C(O)_2$—$Y_1$, —$S(O)_2$—$Y_1$, —S—$Y_1$, cycloalkyl, cycloalkylalkyl, heterocycloalkylalkyl, cycloalkenyl, —C(=N—CN)—$NH_2$, —C(=NH)—$NH_2$, —C(=NH)—NH(alkyl), —$NY_1Y_2$, -alkyl-$NY_1Y_2$, —$C(O)NY_1Y_2$, and —$SO_2NY_1Y_2$, wherein. $Y_1$, $Y_2$ and $Y_3$ can be the same or different and are independently selected from the group consisting of hydrogen, alkyl, aryl, heteroaryl, cycloalkyl, heterocycloalkyl, aralkyl and heteroarylalkyl. "Ring system substituents" on aromatic rings can also be selected from the group consisting of —$SF_5$, —$OSF_5$, —$Si(Y_4)_3$, —$S(O)N(Y_1)(Y_2)$, —C(=$NOY_1$)$Y_2$, —$P(O)(OY_1)(OY_2)$, —$N(Y_1)C(O)Y_2$, —$CH_2$—$N(Y_1)C(O)Y_2$, —$CH_2$—$N(Y_1)C(O)N(Y_1)(Y_3)$, —$N(Y_1)S(O)Y_2$, —$N(Y_1)S(O)_2Y_2$, —$CH_2$—$N(Y_1)S(O)_2Y_2$, —$N(Y_1)S(O)_2N(Y_2)(Y_3)$, —$N(Y_1)S(O)N(Y_2)(Y_3)$, —$N(Y_1)C(O)N(Y_2)(Y_3)$, —$CH_2$—$N(Y_1)C(O)N(Y_2)(Y_3)$, —$N(Y_1)C(O)_2(Y_2)$, —$CH_2$—$N(Y_1)C(O)_2(Y_2)$, —$S(O)Y_1$, =$NOY_1$, and —$N_3$, wherein $Y_1$, $Y_2$ and $Y_3$ are as defined above and each $Y_4$ is independently selected from alkyl, aryl, heteroaryl, cycloalkyl, heterocycloalkyl, aralkyl and heteroarylalkyl. Furthermore, the alkyl, cycloalkyl, aryl, heteroaryl and heterocycloalkyl portions of $Y_1$, $Y_2$ or $Y_3$ can be optionally substituted with 1 or 2 substituents independently selected from the group consisting of halo, OH, —$CF_3$, CN, alkoxy, —$NH_2$, —NH-alkyl, —N(alkyl)$_2$ and Si(alkyl)$_3$. "Ring system substituent" may also mean a single moiety which simultaneously replaces two available hydrogens on two adjacent carbon atoms (one H on each carbon) on a ring system. Examples of such moieties are methylenedioxy, ethylenedioxy, —C(CH$_3$)$_2$— and the like which form moieties such as, for example:

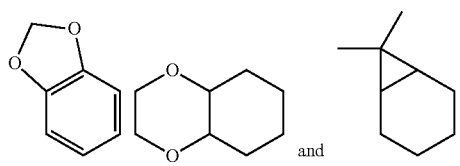

Similarly, a single divalent moiety such as a divalent alkyl chain or a —O—(CH$_2$)$_2$—O— group can simultaneously replace two available hydrogen atoms on one carbon atom on a ring system. An example of such spiro moieties is:

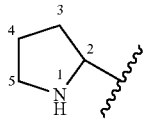

It should be noted that in hetero-atom containing ring systems of this invention, there are no hydroxyl, halo or amino groups on carbon atoms adjacent to a N, O or S, as well as there are no N or S groups on carbon adjacent to another heteroatom. Thus, for example, in the ring:

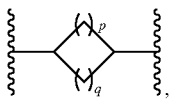

there is no —OH, halo or amino attached directly to carbons marked 2 and 5.

When Z is

examples of such carbocyclic rings are

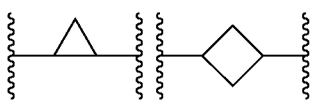

-continued

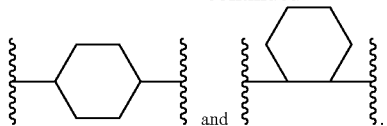

When Z is

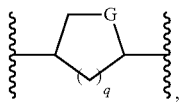

examples of such heterocyclic rings are

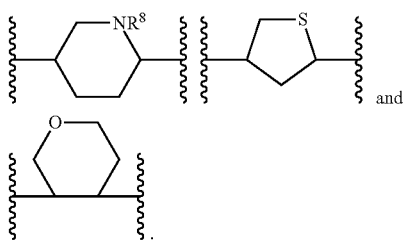

When —N(R$^5$)— and —Z— form a 4 to 7 membered ring, examples of such rings are

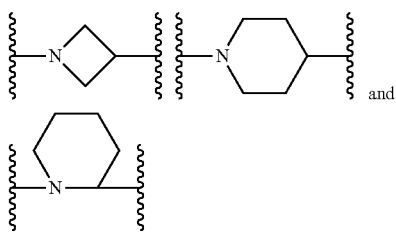

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., alkyl, halo, etc.) occurs more than one time in any constituent or in Formula I or II, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs, solvates and co-crystals of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^{1A}$ wherein Y$^{1A}$ is H, $(C_1-C_6)$alkyl or benzyl, —C(OY$^{2A}$)Y$^{3A}$ wherein Y$^{2A}$ is $(C_1-C_4)$ alkyl and Y$^{3A}$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, —C(Y$^{4A}$)Y$^{5A}$ wherein Y$^{4A}$ is H or methyl and Y$^{5A}$ is mono-N— or di-N,N—$(C_1-C_6)$alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

A co-crystal is a crystalline superstructure formed by combining an active pharmaceutical intermediate with an inert molecule that produces crystallinity to the combined form. Co-crystals are often made between a dicarboxlyic acid such as fumaric acid, succinic acid etc. and a basic amine such as the one represented by compound I or II of this invention in different proportions depending on the nature of the co-crystal. (Rmenar, J. F. et. al. *J Am. Chem. Soc.* 2003, 125, 8456).

"Effective amount" or "therapeutically effective amount" is meant to describe an amount of compound or a composition of the present invention effective as PDE10 inhibitors and thus producing the desired therapeutic, ameliorative, inhibitory or preventative effect.

The compounds of Formula I and II can form salts which are also within the scope of this invention. Reference to a compound of Formula I or II herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I or II contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I or II with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould,

*International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

The compounds of this invention can form esters which are also within the scope of this invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I and II, and salts, solvates, esters, co-crystals and prodrugs thereof, may exist in their tautomeric form (for example, as an amide or imino ether). All such tautomeric forms are contemplated herein as part of the present invention.

The compounds of Formula (I) and (II) may contain asymmetric or chiral centers, and, therefore, exist in different stereoisomeric forms. It is intended that all stereoisomeric forms of the compounds of Formula (I) and (II) as well as mixtures thereof, including racemic mixtures, form part of the present invention. In addition, the present invention embraces all geometric and positional isomers. For example, if a compound of Formula (I) or (II) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) and (II) may be atropisomers (e.g., substituted biaryls) and are considered as part of this invention. Enantiomers can also be separated by use of chiral HPLC column.

It is also possible that the compounds of Formula (I) and (II) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters, co-crystals and prodrugs of the compounds as well as the salts and solvates and esters, co-crystals of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds. Isomers can be prepared using conventional techniques, either by reacting optically pure or optically enriched starting materials or by separating isomers of a compound of Formula I or II. Isomers may also include geometric isomers, e.g., when a double bond is present.

Those skilled in the art will appreciate that for some of the compounds of Formula I and II, one isomer will show greater pharmacological activity than other isomers.

Polymorphic forms of the compounds of Formula I and II, and of the salts, solvates, esters, co-crystals and prodrugs of the compounds of Formula I and II, are intended to be included in the present invention.

In this specification, the term "at least one compound of Formula I (or II)" means that one to three different compounds of Formula I or II may be used in a pharmaceutical composition or method of treatment. Preferably one compound of Formula I or II is used.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

The present invention further includes the compounds of formula I and II in all their isolated forms.

Compounds of Formula I and II are prepared by methods known in the art. A typical reaction scheme for preparing the compounds of Formula I wherein —X—Y— is —C(R$^4$)=N— and the sum of n and m is 2 or 3 is shown in Scheme 1.

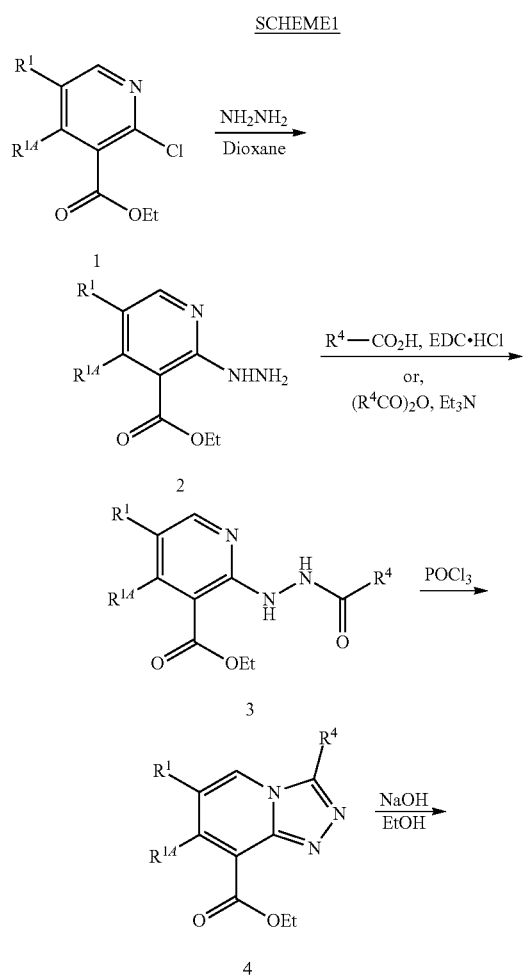

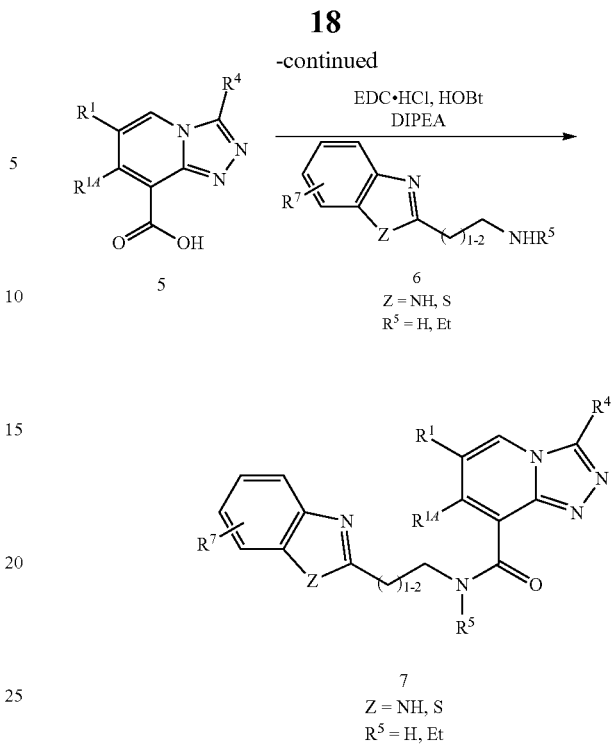

Compounds of Formula I wherein —X—Y— is —N=C(R$^4$)— are prepared by the same process (see Example 2, below).

Compounds of Formula I wherein —X—Y— is —C(R$^4$)=C(R$^4$)— are prepared by methods known in the art.

Compounds of Formula II are prepared by methods known in the art. A typical procedure for preparing compounds of Formula II is shown in Example 8.

In the scheme above and in the following preparative examples, the following abbreviations are used: RT—room temperature; Ac—acetyl; Me—methyl; Et—ethyl; Ph—phenyl; i-Pr—isopropyl; t-Bu—t-butyl; t-Boc—N-tert-butoxycarbonyl; BINAP—2,2'-bis(diphenylphosphino)-1,1'binaphthyl; m-CPBA—m-chloroperoxybenzoic acid; DBU—1,8-diazabicyclo[5.4.0]undec-7-ene; DMF—dimethylformamide; EDC—1-(3-dimethylaminopropyl)-3-ethylcarbodiimide; HOBT—1-hydroxybenzotriazole hydrate; THF—tetrahydrofuran; TFA—trifluoroacetic acid; TLC—thin layer chromatography; DIPEA—diisopropylethylamine; KHMDS—potassium bis(trimethylsilyl)amide.

Where LC/MS data are presented, analyses were performed using an Applied Biosystems API-150 mass spectrometer and Shimadzu SCL-10A LC system. Column: Phenomenex Gemini C18, 5 micron, 50 mm×4.6 mm ID; Gradient: From 90% water, 10% CH$_3$CN and 0.05% TFA, 5 min to 5% water, 95% CH$_3$CN, 0.05% TFA in 5 minutes. MS data were obtained using Agilent Technologies LC/MSD SL or 1100 series LC/MSD mass spectrometer. Retention times refer to Total Ion Current (TIC) unless uv is indicated.

Following are examples of the preparation of intermediates and compounds of Formula I and II.

The [1,2,4]triazolopyridine-8-carboxylic acids 5 in Scheme 1 were synthesized according to the procedure for the synthesis of 3-cyclopropyl-[1,2,4]triazolo[4,3-a]pyridine-8-carboxylic acid 12:

Step 1:

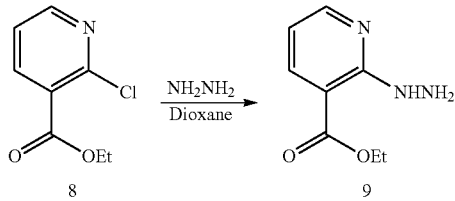

A mixture of ethyl 2-chloronicotinate 8 (2.0 g) and hydrazine (0.4 mL) in 1,4-dioxane (50 mL) was heated to 60° C. for 4 h. The mixture was cooled to RT and concentrated under vacuum to leave a yellow solid (2.8 g) which was purified by column chromatography on silica (elution with $CH_2Cl_2$) to afford 9 (0.75 g) as yellow solid. LCMS: M+1 is 182 at 1.37 and 0.8 min.

Step 2:

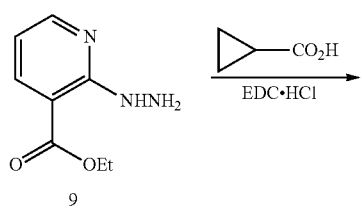

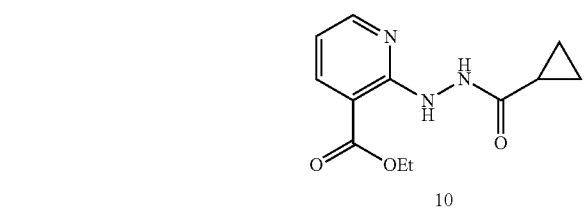

A mixture of 9 (0.75 g) in $CH_2Cl_2$ (20 mL), cyclopropyl carboxylic acid (0.35 g), EDC.HCl (0.94 g), N-methylmorpholine (0.53 mL), and HOBT (10 mg) was stirred at RT for 16 h. The mixture was diluted with $CH_2Cl_2$ and extracted with $H_2O$ (3×30 mL). The organic layer was dried over $MgSO_4$, filtered, and concentrated under vacuum to afford 10 (1.0 g) as a yellow solid which was directly used in the next step without further purification. LCMS: M+1 is 250 at 1.70, 0.82 min.

Preparation of 10-1:

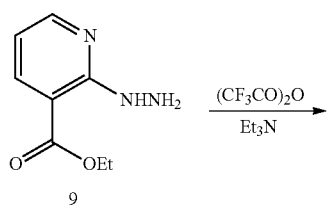

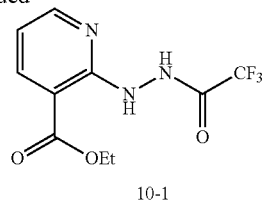

To a cold (0° C.), stirred mixture of 9 (10.0 g) and $Et_3N$ (11.2 g) in anhydrous $CH_2Cl_2$ (60 mL) was added trifluoroacetic anhydride (12.7 g) dropwise over 30 min via an addition funnel. After the addition was complete, the ice-bath was removed and the mixture was stirred at RT for 3 h before being quenched with $H_2O$ (200 mL). The organic layer was separated and the aqueous layer was extracted with $CH_2Cl_2$ (3×100 mL). The combined organic layers were dried over $Mg_2SO_4$, filtered, and concentrated under vacuum to afford 10-1 as an orange solid which was used directly in the next step without further purification. LCMS: M+1 is 278.2 at 3.1 min.

Step 3:

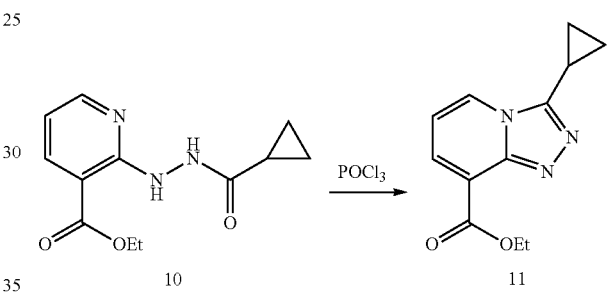

To a stirred solution of 10 (0.76 g) in 1,2-dichloroethane (15 mL) was added $POCl_3$ (1 mL) and the mixture was heated under reflux for 20 h. The mixture was cooled to RT and concentrated under vacuum to leave a residue. The residue was redissolved in EtOAc and washed with a saturated aqueous solution of $NaHCO_3$. The organic layer was dried over $Mg_2SO_4$, filtered, and concentrated under vacuum to afford 11 (0.37 g) as a tan solid. LCMS: M+1 is 232 at 1.56, 12.8, 0.88 min.

Step 4:

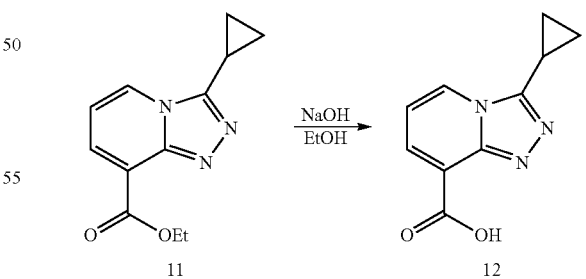

To a cold (0° C.), stirred solution of ester 11 (0.36 g) in EtOH (7 mL) was added NaOH (1 mL of 2.5 N aqueous solution) and the mixture was slowly warmed to RT over 3 h. The reaction was quenched with conc. HCl until pH 2-3 and concentrated under vacuum to leave a solid. Water was added and the solid was filtered to afford acid 12 (0.17 g) as a white solid.

The following compounds were prepared in the similar manner.
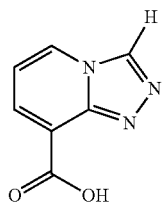
12-1
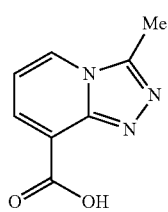
12-2
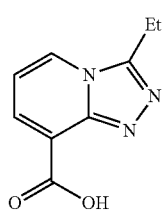
12-3
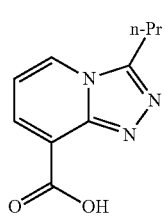
12-4
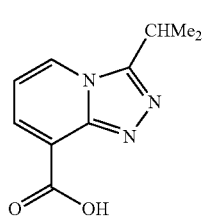
12-5
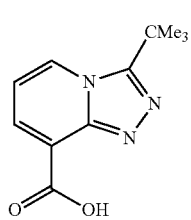
12-6
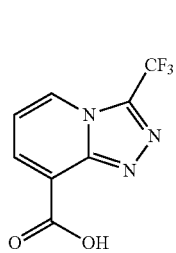
12-7
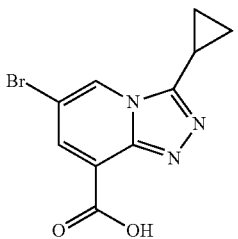
12-8
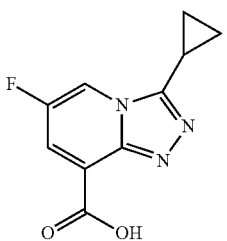
12-9
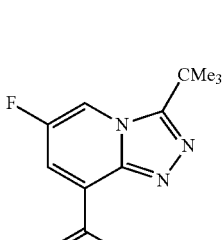
12-10
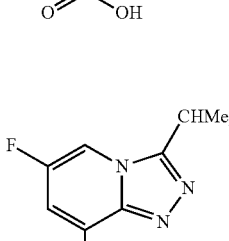
12-11
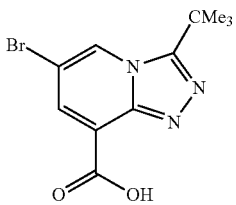
12-12
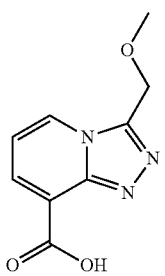
12-13

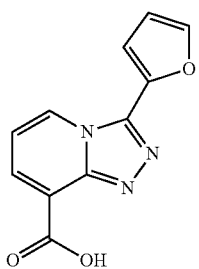

12-14

The (benzimidazol-2-yl)ethanamines 6 in Scheme 1 are commercially available or are synthesized according to the represented procedure for the synthesis of 2-(5,6-dichloro-1H-benzo[d]imidazol-2-yl)ethanamine 16.

Step 1:

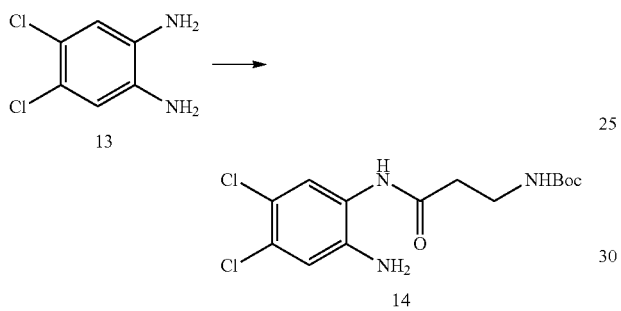

To a cold (−20° C.), stirred solution of β-N-Boc-alanine (1.81 g) in DMF (10 mL) was added N-methylmorpholine (1 mL). The mixture was stirred for 10 min at −20° C. followed by the addition of isobutyl chloroformate (1.2 mL). After being stirred for additional 10 min, 4,5-dichlorophenylene diamine (13) (1.70 g) was added to the reaction mixture. The resulting mixture was slowly warmed to RT over 1 h and stirred for 18 h. The reaction mixture was concentrated under vacuum and redissolved in EtOAc. The organic layer was washed with H₂O, an aqueous solution of NaHCO₃, then brine. The organic layer was dried over MgSO₄, filtered and concentrated under vacuum to afford 14 (2.73 g) as a dark brown foam. LCMS: M+1 is 348 at 3.75 min.

Step 2:

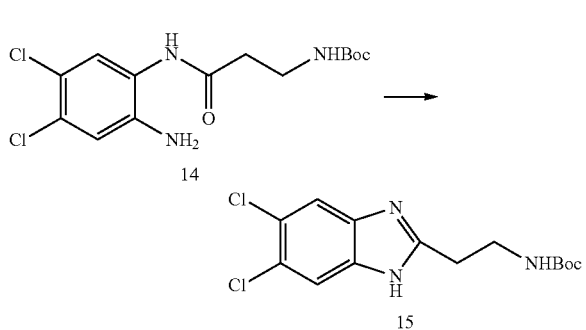

A mixture of compound 14 (2.72 g) and glacial acetic acid (10 mL) was heated at 65° C. for 3 h. The mixture was cooled to RT and concentrated under vacuum to leave dark oil (2.71 g) which was further purified by preparative TLC (20, 1000µ) on silica gel (elution with dichloromethane:MeOH 9:1) to afford 15 (1.10 g). LCMS: M+1 is 330 at 2.61 min.

Step 3:

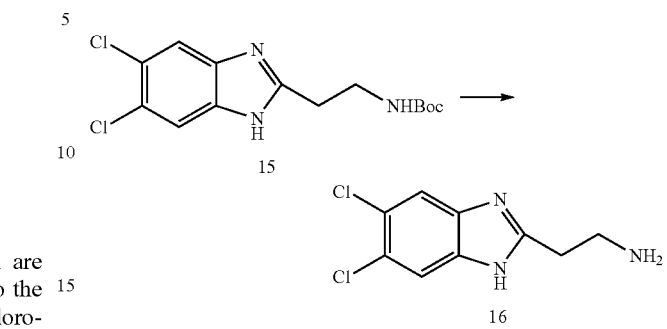

To a stirred solution of compound 15 (0.51 g) in CH₂Cl₂ (1 mL) was added TFA (1 mL) and the mixture was stirred at RT for 1 h. The reaction mixture was concentrated under vacuum to leave an oil (0.45 g) which was re-dissolved in CH₂Cl₂. The organic layer was then washed with a saturated aqueous solution K₂CO₃, dried over MgSO₄, filtered, and concentrated under vacuum to afford 16 (0.22 g) as a yellow solid. LCMS: M+1 is 230 at 2.08, 1.57, 1.03.

The following compounds were prepared in the similar manner.

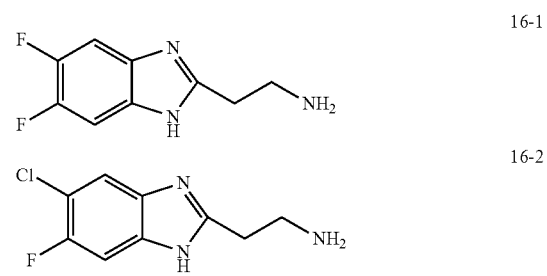

EXAMPLE 1

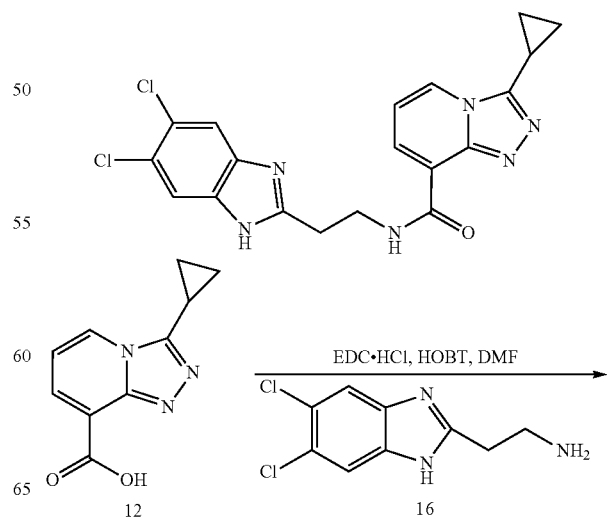

-continued

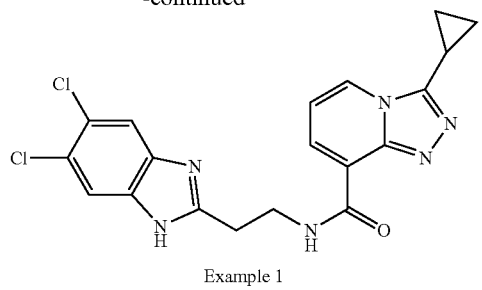
Example 1

A mixture of acid 12 (150 mg), amine 16 (210 mg), EDC.HCl (150 mg), and HOBT (120 mg) in DMF (8 mL) was stirred at RT for 16 h. The reaction was quenched with H$_2$O and extracted with CH$_2$Cl$_2$ (3×20 mL). The organic layer was then dried over MgSO$_4$, filtered and concentrated under vacuum to leave a residue which was purified by preparative TLC on silica gel (elution with 19:1 CH$_2$Cl$_2$:MeOH) to yield Example 1 (105 mg) as an off-white solid. LCMS: M+1 is 415 at 2.46 min.

The following compounds were prepared in the similar manner.

| Ex. No. | Structure | MW | LCMS M+1 | R$_t$ |
|---|---|---|---|---|
| 1A | 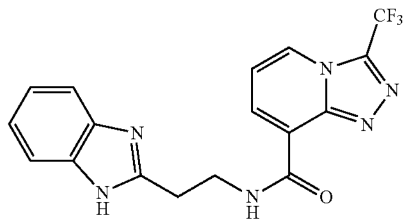 [SMILES: O=C(NCCc1nc2ccccc2[nH]1)c1cccn2c(C(F)(F)F)nnc12] | 374 | 375 | 2.13 |
| 1B | 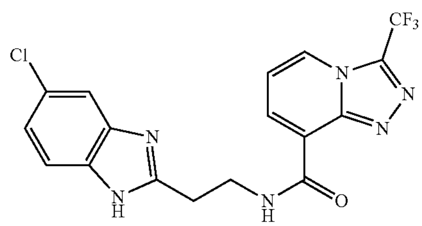 [SMILES: O=C(NCCc1nc2cc(Cl)ccc2[nH]1)c1cccn2c(C(F)(F)F)nnc12] | 408 | 409 | 2.44 |
| 1C | 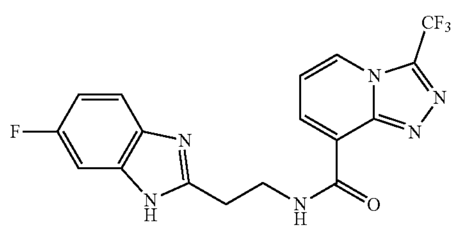 [SMILES: O=C(NCCc1nc2ccc(F)cc2[nH]1)c1cccn2c(C(F)(F)F)nnc12] | 392 | 393 | 2.33 |
| 1D | 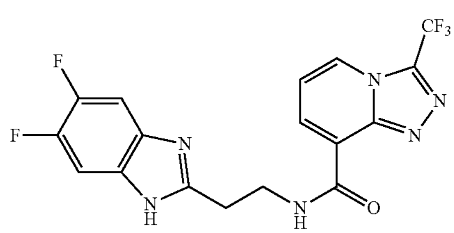 [SMILES: O=C(NCCc1nc2cc(F)c(F)cc2[nH]1)c1cccn2c(C(F)(F)F)nnc12] | 410 | 411 | 2.25 |
| 1E | 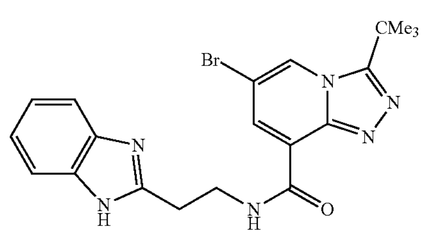 | 441 | 442 | 2.60 |

-continued
| Ex. No. | Structure | MW | LCMS M + 1 | $R_f$ |
|---|---|---|---|---|
| 1F | 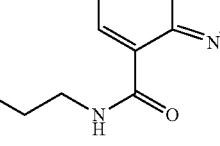 | 459 | 460 | 2.66 |
| 1G | 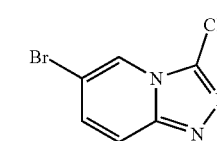 | 475 | 476 | 2.94 |
| 1H | 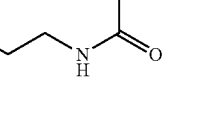 | 477 | 478 | 2.74 |
| 1I | 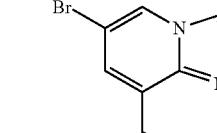 | 425 | 426 | 2.24 |
| 1J | 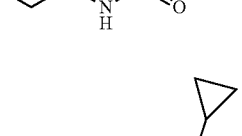 | 461 | 461 | 2.50 |
| 1K | 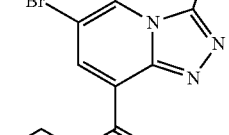 | 416 | 417 | 2.50 |

-continued
| Ex. No. | Structure | MW | LCMS M+1 | $R_t$ |
|---|---|---|---|---|
| 1L | 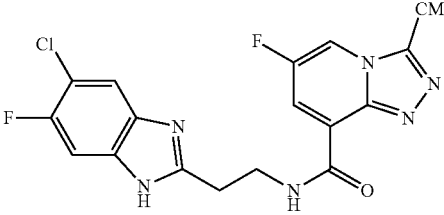 | 432 | 433 | 2.64 |
| 1M | 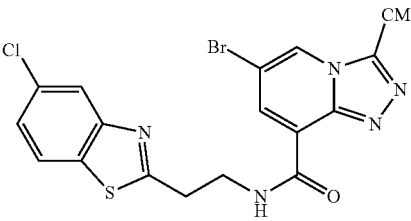 | 492 | 494 | 5.40 |
| 1N | 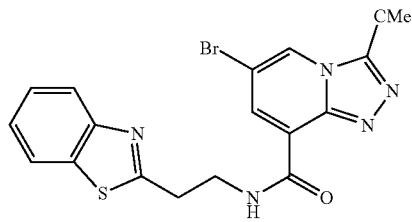 | 458 | 460 | 4.85 |
| 1O | 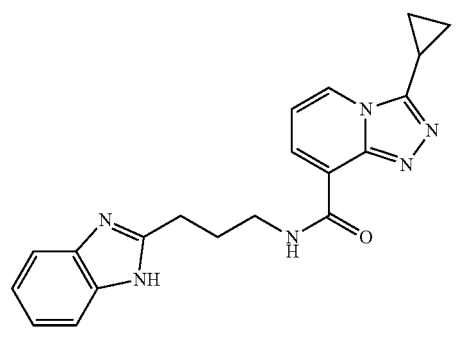 [SMILES: O=C(NCCCc1nc2ccccc2[nH]1)c1cccn2c(C3CC3)nnc12] | 360 | 361 | 0.73, 1.53, 1.68 |
| 1P | 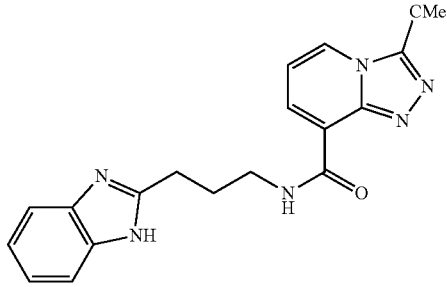 | 376 | 377 | 2.40 |

-continued
| Ex. No. | Structure | MW | LCMS M + 1 | $R_t$ |
|---|---|---|---|---|
| 1Q | 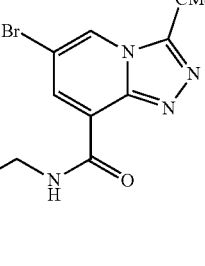 | 455 | 455 | 2.40 |
| 1R | 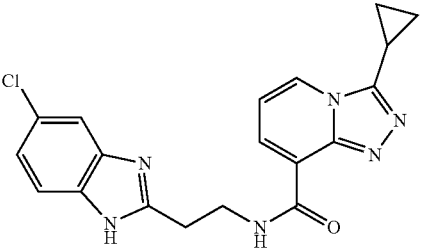 [SMILES: O=C(NCCc1nc2cc(Cl)ccc2[nH]1)c1cccn2c(C3CC3)nnc12] | 380 | 381 | 2.13 |
| 1S | 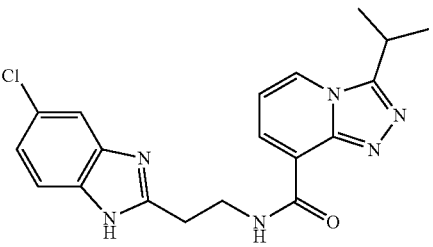 [SMILES: CC(C)c1nnc2c(C(=O)NCCc3nc4cc(Cl)ccc4[nH]3)cccn12] | 382 | 383 | 2.15 |
| 1T | 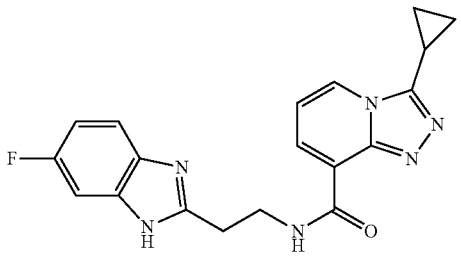 [SMILES: O=C(NCCc1nc2ccc(F)cc2[nH]1)c1cccn2c(C3CC3)nnc12] | 364 | 365 | 1.91 |
| 1U | 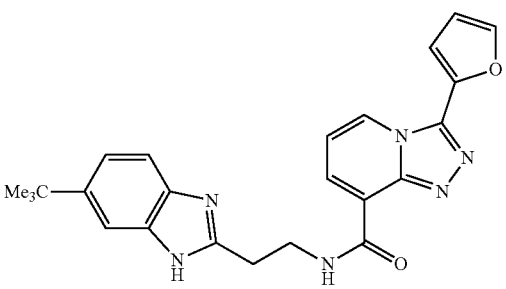 | 428 | 429 | 2.70 |

-continued
| Ex. No. | Structure | MW | LCMS M + 1 | R$_t$ |
|---|---|---|---|---|
| 1V | 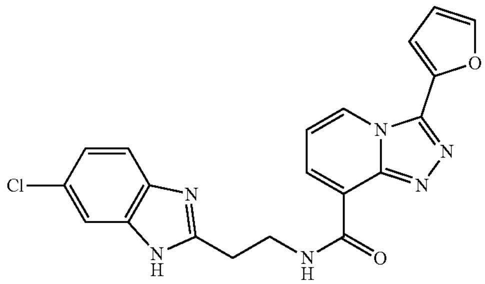 [SMILES: O=C(NCCc1nc2ccc(Cl)cc2[nH]1)c1cccn2c(-c3ccco3)nnc12] | 406 | 407 | 2.34 |
| 1W | 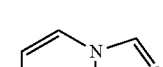 | 340 | 341 | 1.87 |
| 1X | 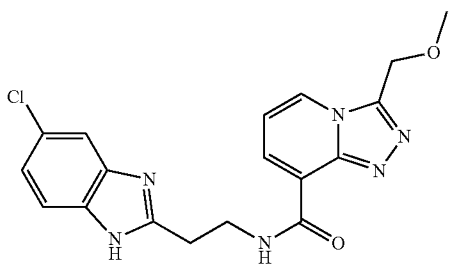 [SMILES: COCc1nnc2c(C(=O)NCCc3nc4cc(Cl)ccc4[nH]3)cccn12] | 384 | 385 | 2.09 |
| 1Y | 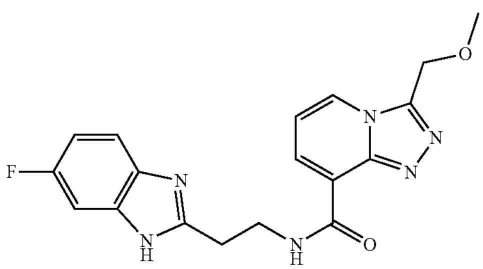 [SMILES: COCc1nnc2c(C(=O)NCCc3nc4ccc(F)cc4[nH]3)cccn12] | 368 | 369 | 1.90 |
| 1Z | 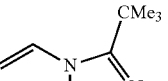 | 396 | 397 | 2.41 |
| 1AA | 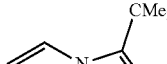 | 380 | 381 | 2.24 |

| Ex. No. | Structure | MW | LCMS M + 1 | R_t |
|---|---|---|---|---|
| 1BB | 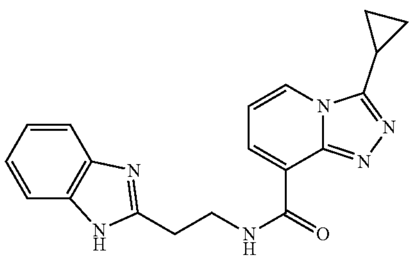 [SMILES: O=C(NCCc1nc2ccccc2[nH]1)c1cccn2c(C3CC3)nnc12] | 346 | 347 | 2.49 |
| 1CC | 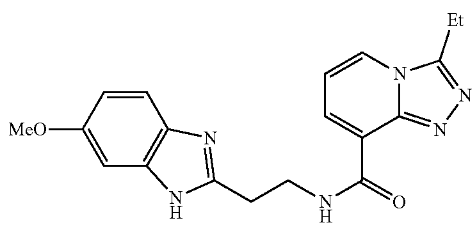 [SMILES: CCc1nnc2c(C(=O)NCCc3nc4ccc(OC)cc4[nH]3)cccn12] | 364 | 365 | 2.35 |
| 1DD | 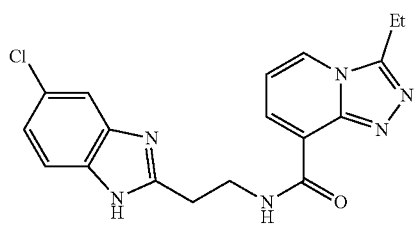 | 368 | 369 | 2.66 |
| 1EE | 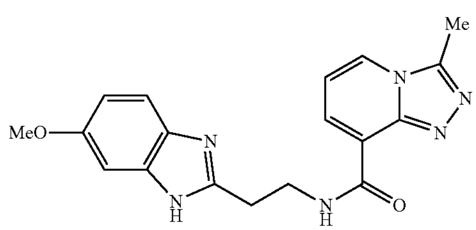 | 350 | 351 | 2.37 |
| 1FF | 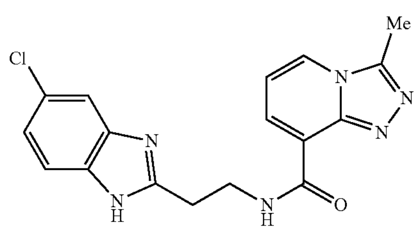 | 354 | 355 | 2.51 |
| 1GG | 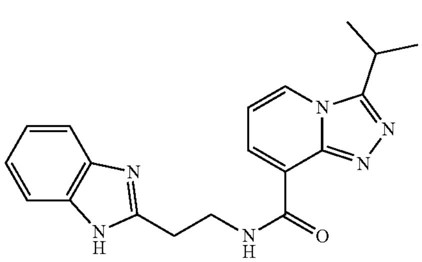 [SMILES: CC(C)c1nnc2c(C(=O)NCCc3nc4ccccc4[nH]3)cccn12] | 348 | 349 | 1.95 |

-continued

| Ex. No. | Structure | MW | LCMS M + 1 | R$_t$ |
|---|---|---|---|---|
| 1HH | 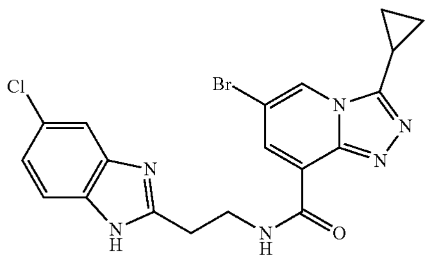 [SMILES: O=C(NCCc1nc2cc(Cl)ccc2[nH]1)c1cc(Br)cn2c(C3CC3)nnc12] | 459 | 461 | 2.43 |
| 1II | 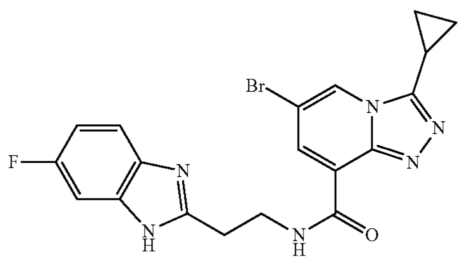 [SMILES: O=C(NCCc1nc2ccc(F)cc2[nH]1)c1cc(Br)cn2c(C3CC3)nnc12] | 443 | 445 | 2.31 |
| 1JJ | 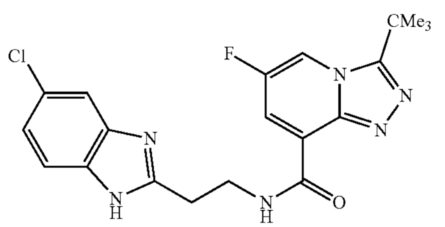 | 414 | 415 | 2.37 |
| 1KK | 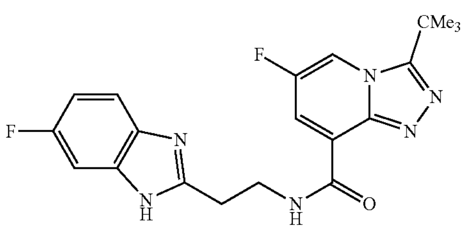 | 398 | 399 | 2.24 |
| 1LL | 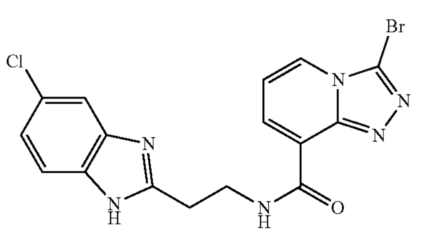 [SMILES: O=C(NCCc1nc2cc(Cl)ccc2[nH]1)c1cccn2c(Br)nnc12] | 419 | 421 | 2.06 |
| 1MM | 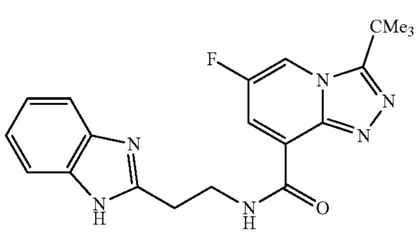 | 380 | 381 | 2.30 |

-continued
| Ex. No. | Structure | MW | LCMS M + 1 | R$_t$ |
|---|---|---|---|---|
| 1NN | 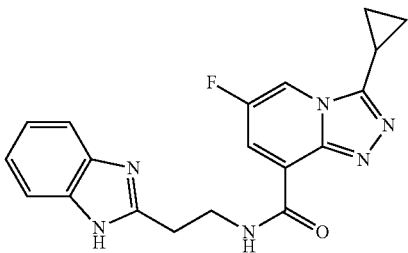 [SMILES: O=C(NCCc1nc2ccccc2[nH]1)c1cc(F)cn2c(C3CC3)nnc12] | 364 | 365 | 2.06 |
| 1OO | 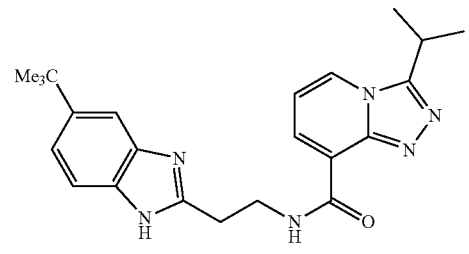 | 404 | 405 | 2.62 |
| 1PP | 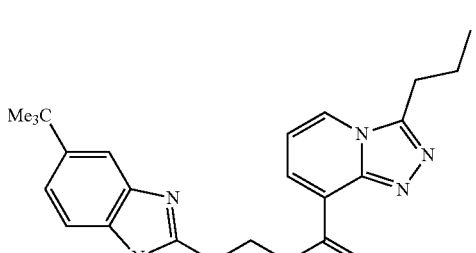 | 404 | 405 | 2.51 |
| 1QQ | 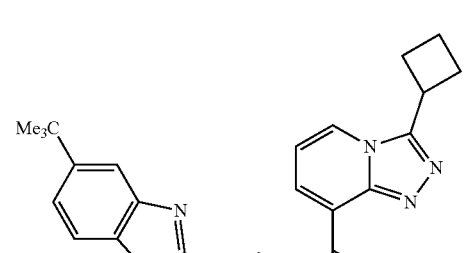 | 416 | 417 | 2.76 |
| 1RR | 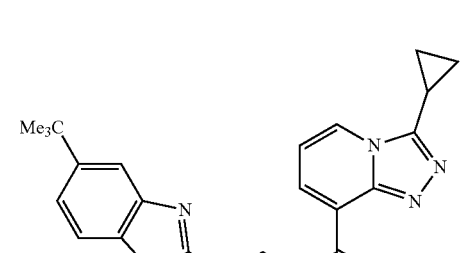 | 402 | 403 | 2.51 |

-continued
| Ex. No. | Structure | MW | LCMS M + 1 | R_t |
|---|---|---|---|---|
| 1SS | 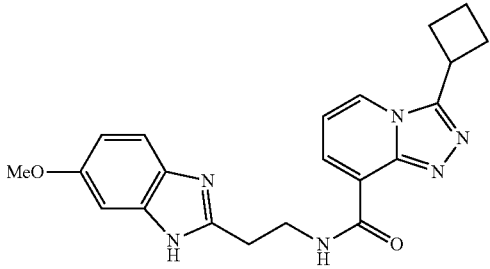 [SMILES: COc1ccc2nc(CCNC(=O)c3cccn4c(C5CCC5)nnc34)[nH]c2c1] | 390 | 391 | 3.20 |
| 1TT | 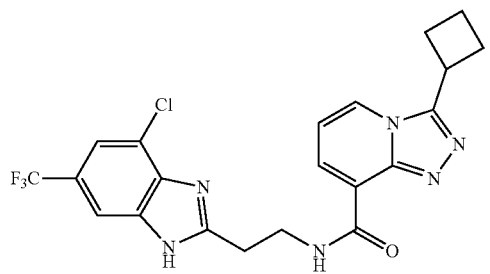 [SMILES: O=C(NCCc1nc2c(Cl)cc(C(F)(F)F)cc2[nH]1)c1cccn2c(C3CCC3)nnc12] | 462 | 463 | 4.08 |
| 1UU | 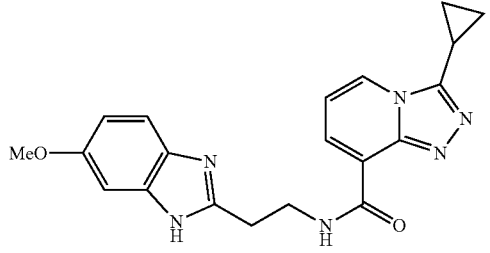 [SMILES: COc1ccc2nc(CCNC(=O)c3cccn4c(C5CC5)nnc34)[nH]c2c1] | 376 | 377 | 2.91 |
| 1VV | 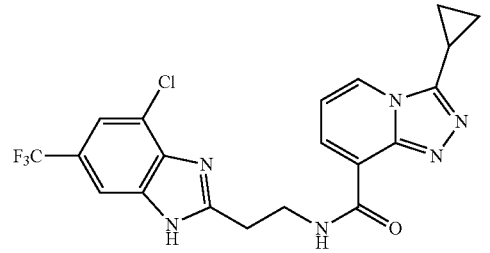 [SMILES: O=C(NCCc1nc2c(Cl)cc(C(F)(F)F)cc2[nH]1)c1cccn2c(C3CC3)nnc12] | 448 | 449 | 3.90 |
| 1WW | 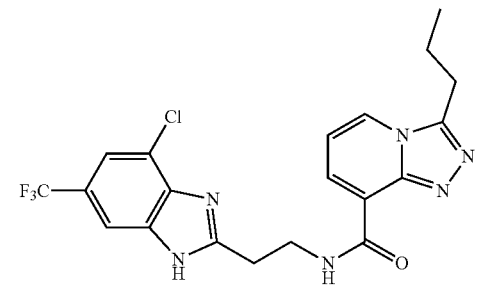 [SMILES: CCCc1nnc2c(C(=O)NCCc3nc4c(Cl)cc(C(F)(F)F)cc4[nH]3)cccn12] | 450 | 451 | 4.01 |

| Ex. No. | Structure | MW | LCMS M + 1 | R_t |
|---|---|---|---|---|
| 1XX | 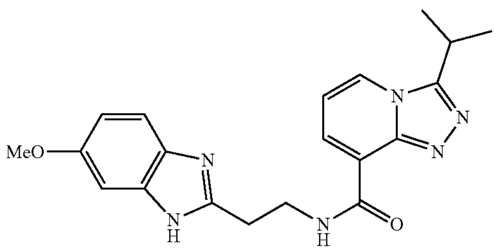 [SMILES: COc1ccc2nc(CCNC(=O)c3cccn4c(C(C)C)nnc34)[nH]c2c1] | 378 | 379 | 2.97 |
| 1YY | 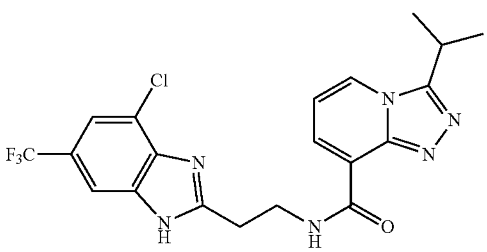 [SMILES: CC(C)c1nnc2c(C(=O)NCCc3nc4c(Cl)cc(C(F)(F)F)cc4[nH]3)cccn12] | 450 | 451 | 3.95 |
| 1ZZ | 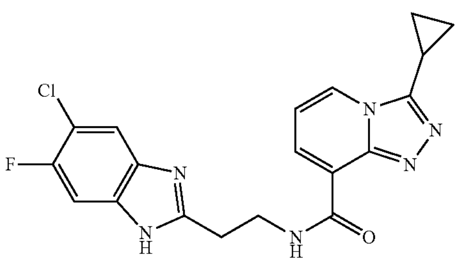 [SMILES: O=C(NCCc1nc2cc(Cl)c(F)cc2[nH]1)c1cccn2c(C3CC3)nnc12] | 398 | 399 | 2.32 |
| 1AAA | 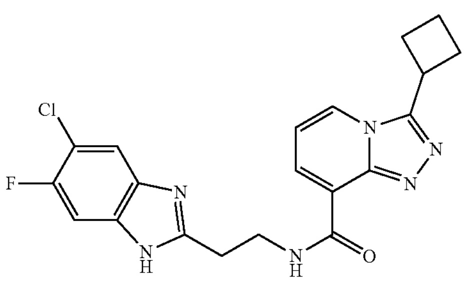 [SMILES: O=C(NCCc1nc2cc(Cl)c(F)cc2[nH]1)c1cccn2c(C3CCC3)nnc12] | 412 | 413 | 2.50 |
| 1BBB | 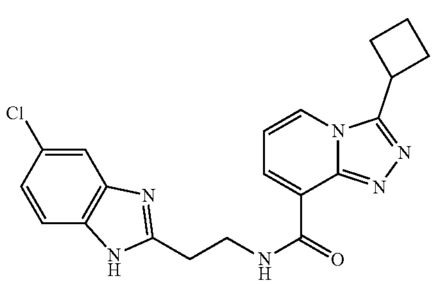 [SMILES: O=C(NCCc1nc2cc(Cl)ccc2[nH]1)c1cccn2c(C3CCC3)nnc12] | 394 | 395 | 2.37 |

-continued
| Ex. No. | Structure | MW | LCMS M + 1 | R_t |
|---|---|---|---|---|
| 1CCC | 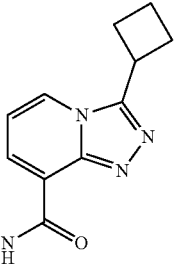 | 378 | 379 | 2.21 |
| 1DDD | 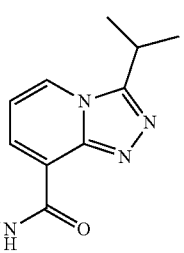 | 400 | 401 | 2.22 |
| 1EEE | 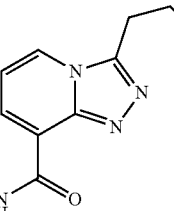 | 400 | 401 | 2.25 |
| 1FFF | 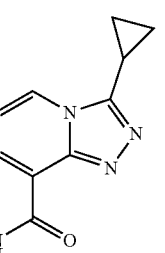 | 398 | 399 | 2.31, 2.07, 0.8 |
| 1GGG | 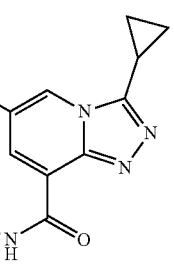 | 382 | 383 | 2.10, 1.94 |
| 1HHH | 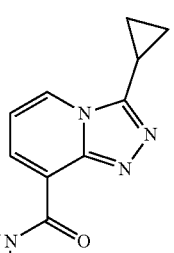 | 392 | 393 | 3.07 |

-continued

| Ex. No. | Structure | MW | LCMS M + 1 | R$_f$ |
|---|---|---|---|---|
| 1III | 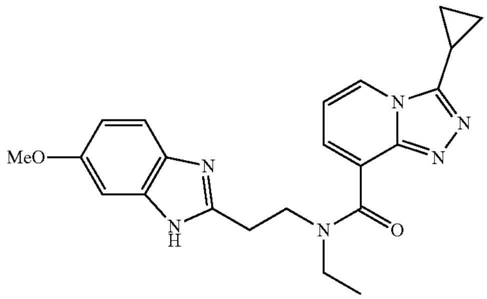 [SMILES: CCN(CCc1nc2ccc(OC)cc2[nH]1)C(=O)c1cccn2c(C3CC3)nnc12] | 404 | 405 | 3.07 |
| 1JJJ | 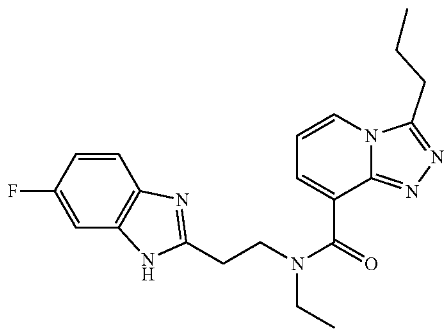 [SMILES: CCCc1nnc2c(C(=O)N(CC)CCc3nc4ccc(F)cc4[nH]3)cccn12] | 394 | 395 | 3.15 |
| 1KKK | 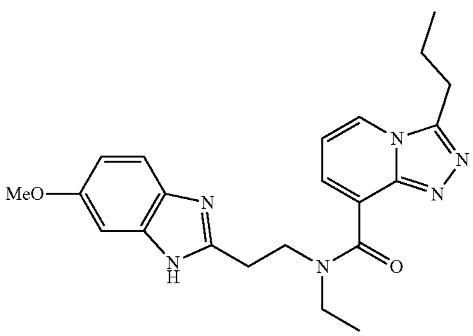 [SMILES: CCCc1nnc2c(C(=O)N(CC)CCc3nc4ccc(OC)cc4[nH]3)cccn12] | 406 | 407 | 3.12 |
| 1LLL | 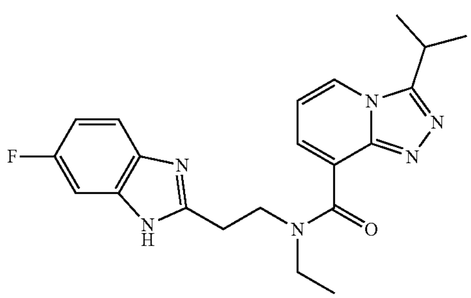 [SMILES: CCN(CCc1nc2ccc(F)cc2[nH]1)C(=O)c1cccn2c(C(C)C)nnc12] | 394 | 395 | 3.15 |
| 1MMM | 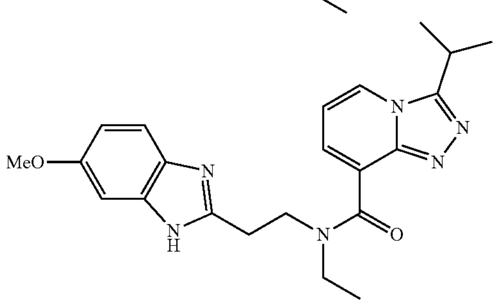 | 406 | 407 | 3.17 |

EXAMPLE 2

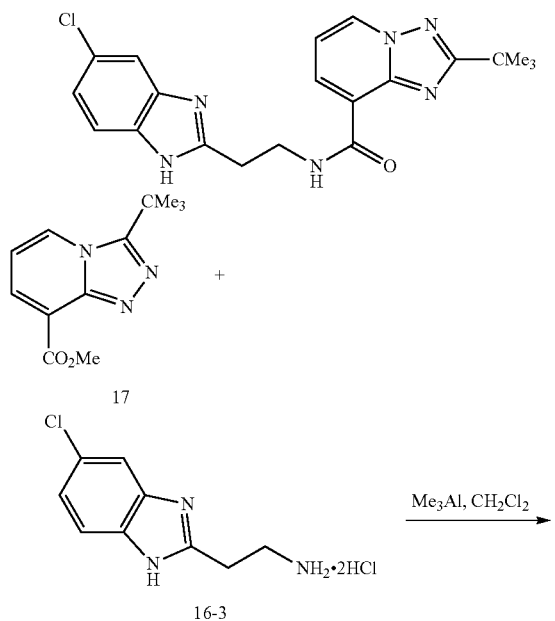

To a cold (0° C.), stirred solution of 2-(5-chloro-1H-benzoimidazol-2-yl)-ethylamine dihydrochloride (16-3) (0.49 g) in $CH_2Cl_2$ (7 mL) was added DIPEA (0.23 g) dropwise. After being stirred for 20 min at 0° C., $Me_3Al$ (1.0 mL of 2.0 M solution in toluene) was added dropwise. The mixture was stirred at RT for 1 h and then cooled back to 0° C. when ester 17 (100 mg) was added in one portion. The mixture was stirred at RT overnight before being cooled to 0° C. The reaction was quenched with a saturated aqueous solution of Na—K-tartrate and diluted with $H_2O$. The resulting solution was extracted with $CH_2Cl_2$ (3×20 mL). The combined organic layers were dried over $MgSO_4$, filtered and concentrated under vacuum to leave a residue which was purified by column chromatography on silica (elution with 0 to 8% MeOH in $CH_2Cl_2$) to afford 1Z (28 mg) and Example 2 (7 mg).

Using a similar procedure, the following compounds were prepared:

| Ex. No. | Structure | MW | LCMS M+1 | $R_t$ |
|---|---|---|---|---|
| 2A | 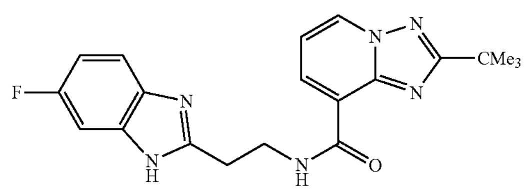 | 380 | 381 | 2.57 |
| 2B | 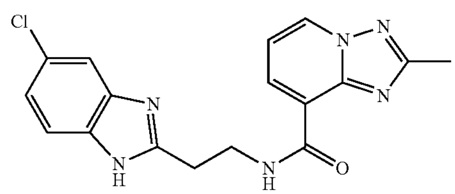 [SMILES: Cc1nc2c(C(=O)NCCc3nc4cc(Cl)ccc4[nH]3)cccn2n1] | 354 | 355 | 2.13 |
| 2C | 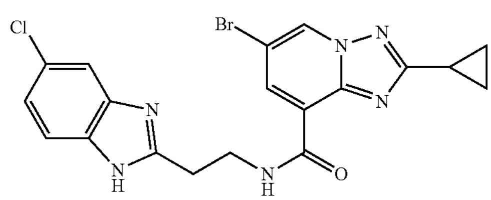 [SMILES: O=C(NCCc1nc2cc(Cl)ccc2[nH]1)c1cc(Br)cn2nc(C3CC3)nc12] | 459 | 461 | 2.67 |
| 2D | 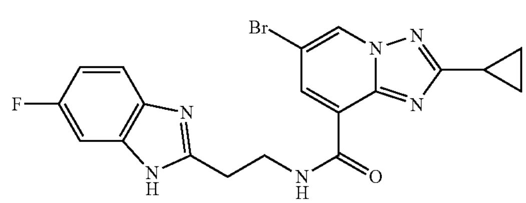 [SMILES: O=C(NCCc1nc2ccc(F)cc2[nH]1)c1cc(Br)cn2nc(C3CC3)nc12] | 443 | 445 | 2.57 |

-continued
| Ex. No. | Structure | MW | LCMS M + 1 | $R_t$ |
|---|---|---|---|---|
| 2E | 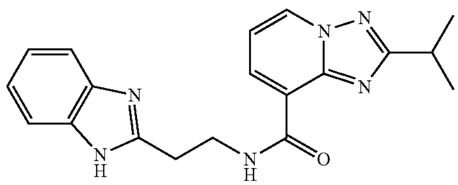 [SMILES: CC(C)c1nc2c(C(=O)NCCc3nc4ccccc4[nH]3)cccn2n1] | 348 | 349 | 2.12 |
| 2F | 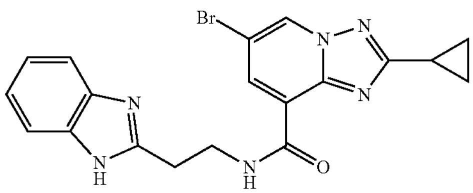 [SMILES: O=C(NCCc1nc2ccccc2[nH]1)c1cc(Br)cn2nc(C3CC3)nc12] | 425 | 427 | 2.59 |
| 2G | 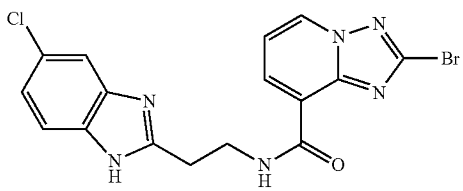 [SMILES: O=C(NCCc1nc2cc(Cl)ccc2[nH]1)c1cccn2nc(Br)nc12] | 419 | 421 | 2.23 |
EXAMPLE 3
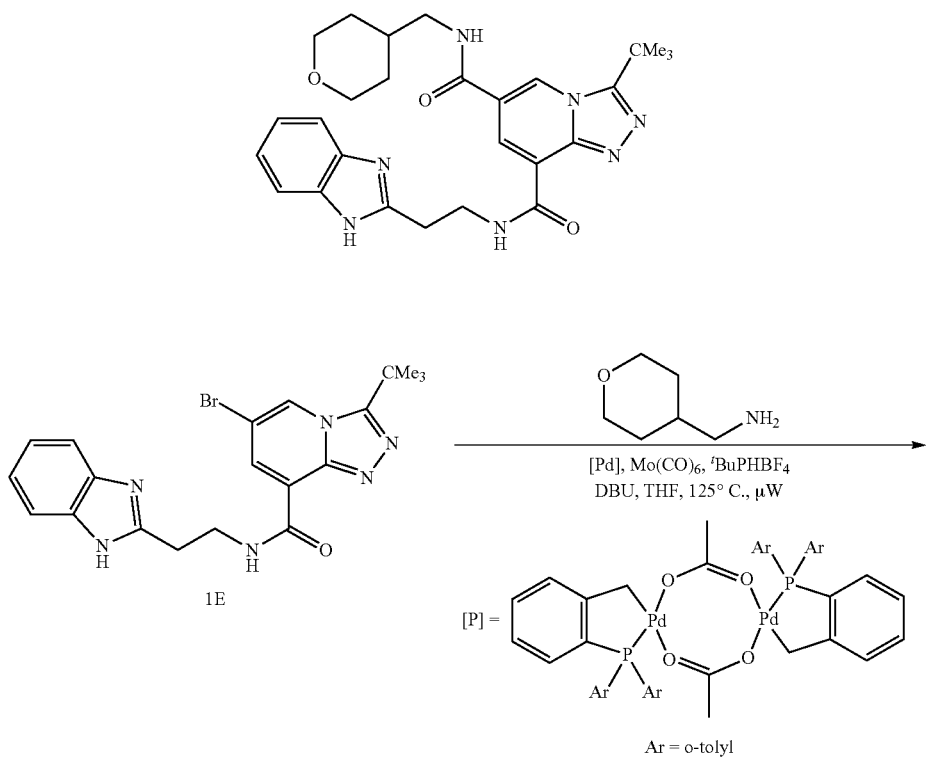

-continued

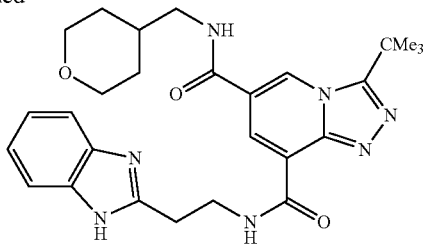

Example 3

A mixture of 1E (50 mg), amine (19.5 mg), DBU (11.6 mg), Mo(CO)₆ (15 mg), t-Bu₃PHBF₄ (1 mg), and [2-(di-(1-tolyl-phosphino)-benzyl]di-palladium(II) (1.2 mg) in THF (1 mL) was heated to 125° C. in microwave for 20 min. The reaction mixture was concentrated under vacuum to leave a residue which was purified by preparative TLC (elution with 5:1 CH₂Cl₂:MeOH) to afford Example 3 (12.2 mg) as an off-white solid. LCMS: M+1 is 504 at 2.44 min.

Using a similar procedure with the appropriate amine, the following compounds were prepared:

| Ex. No. | Structure | MW | LCMS M + 1 | R_t |
|---|---|---|---|---|
| 3A | 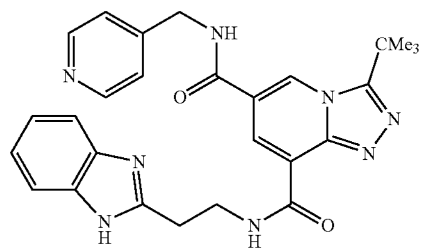 | 496 | 497 | 2.05 |
| 3B | 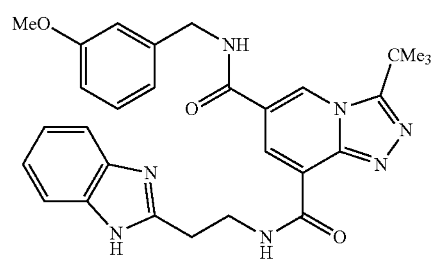 | 525 | 526 | 2.88 |
| 3C | 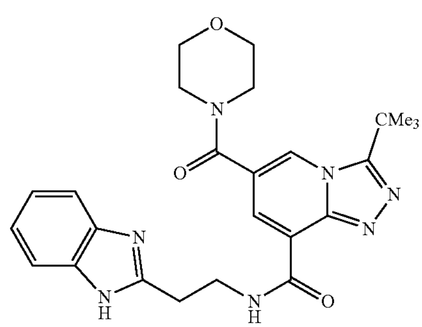 | 475 | 476 | 2.42 |
| 3D | 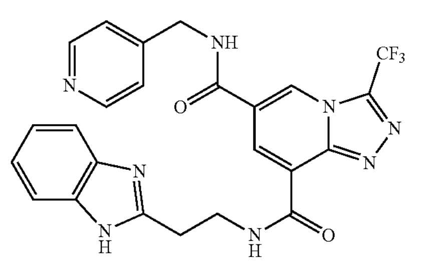 [SMILES: O=C(NCc1ccncc1)c1cc(C(=O)NCCc2nc3ccccc3[nH]2)c2nnc(C(F)(F)F)n2c1] | 508 | 509 | 2.21 |

| Ex. No. | Structure | MW | LCMS M + 1 | $R_t$ |
|---|---|---|---|---|
| 3E | 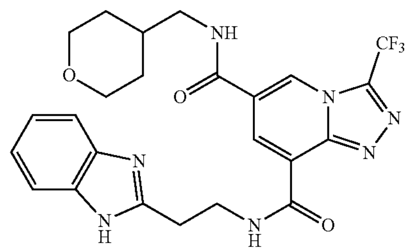 [SMILES: O=C(NCC1CCOCC1)c1cc(C(=O)NCCc2nc3ccccc3[nH]2)c2nnc(C(F)(F)F)n2c1] | 515 | 516 | 2.69 |

EXAMPLE 4

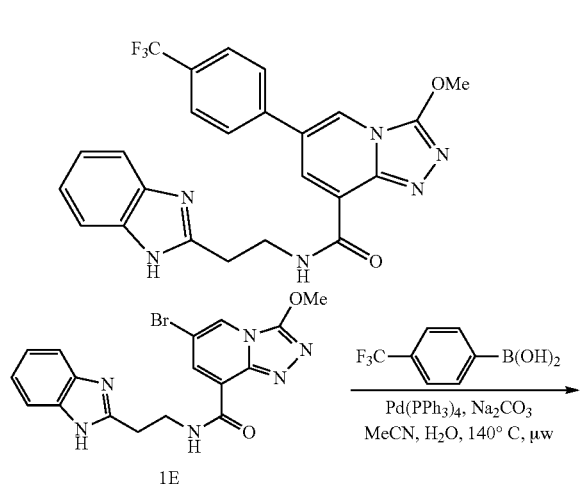

A mixture of 1E (60 mg), 4-(trifluoromethyl)phenylboronic acid (77.5 mg), Pd(PPh$_3$)$_4$ (15.7 mg), and Na$_2$CO$_3$ (72 mg) in MeCN (1 mL) and H$_2$O (0.25 mL) was heated to 140° C. in microwave for 15 min. The mixture was directly poured into a column and purified by column chromatography on silica gel (elution with 30:1 CH$_2$Cl$_2$:MeOH) to afford Example 4 (44.9 mg) as a yellow solid. LCMS: M+1 is 507 at 3.26 min.

Using a similar procedure, the following compounds were prepared:

| Ex. No. | Structure | MW | LCMS M + 1 | $R_t$ |
|---|---|---|---|---|
| 4A | 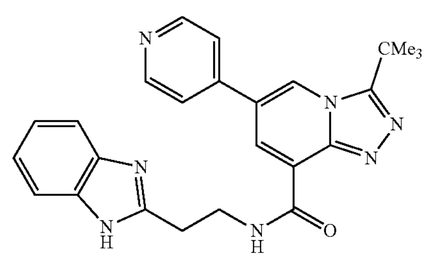 | 439 | 440 | 2.09 |
| 4B | 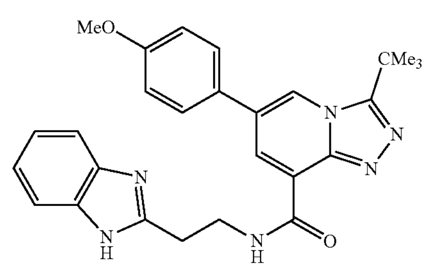 | 468 | 459 | 2.91 |

| Ex. No. | Structure | MW | LCMS M + 1 | R$_t$ |
|---------|-----------|-----|------------|-------|
| 4C | 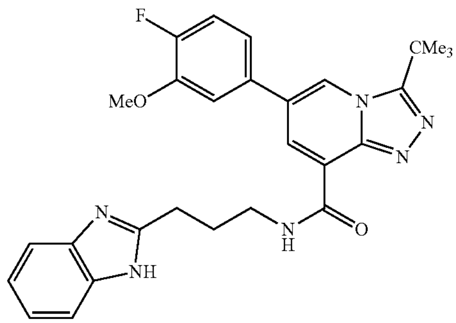 | 500 | 501 | 3.05 |
| 4D | 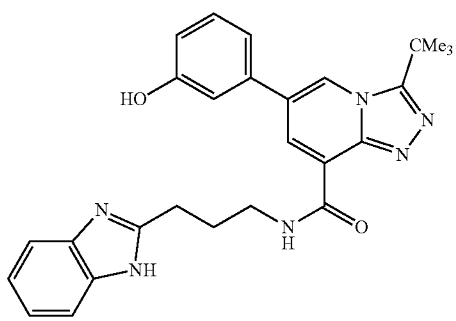 | 468 | 469 | 2.64 |
| 4E | 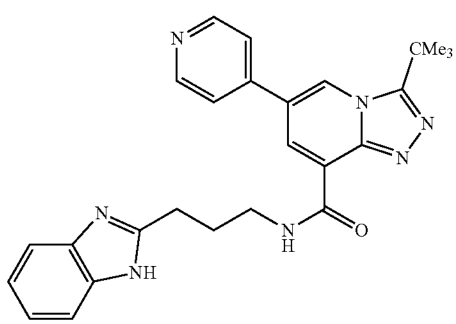 | 453 | 454 | 1.96 |
| 4F | 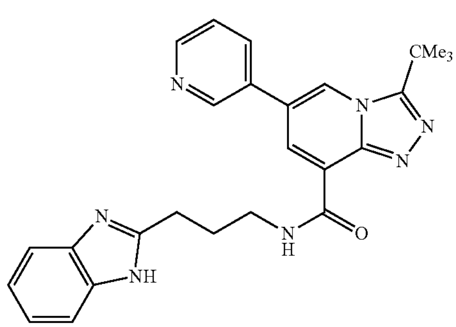 | 453 | 454 | 2.08 |

| Ex. No. | Structure | MW | LCMS M + 1 | $R_t$ |
|---|---|---|---|---|
| 4G | 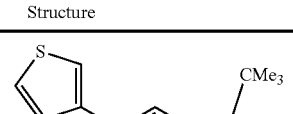 | 458 | 459 | 2.85 |

EXAMPLE 5

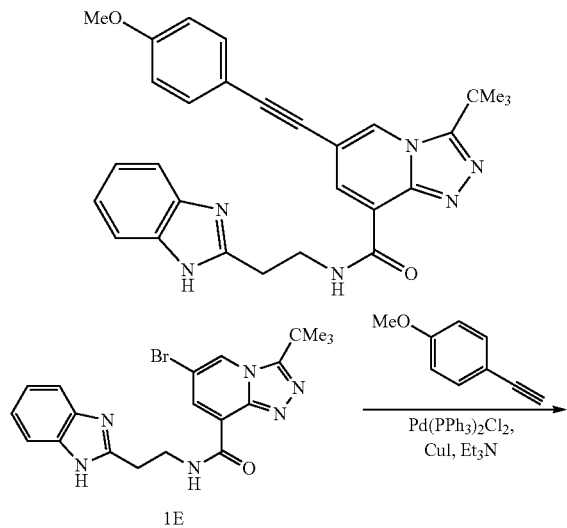

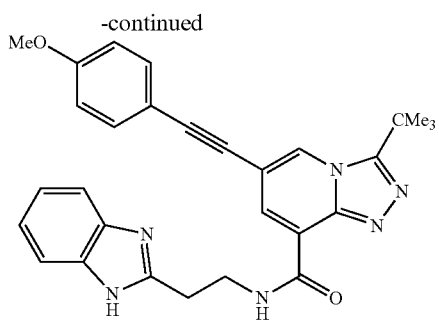

Example 5

To a stirred mixture of 1E (60 mg), Pd(PPh$_3$)$_2$Cl$_2$ (4.8 mg), CuI (1.3 mg), and Et$_3$N (206 mg) in THF (1 mL) was added 4-ethynyl anisole (36 mg). The mixture was stirred at RT for 3 days. The reaction was quenched with H$_2$O and extracted with CH$_2$Cl$_2$ (3×10 mL). The combined organic layers were dried over Mg$_2$SO$_4$, filtered, and concentrated under vacuum to leave a residue which was purified by column chromatography on silica (elution with 20:1 CH$_2$Cl$_2$:MeOH) to yield Example 5 (37 mg) as a yellow solid. LCMS: M+1 is 493 at 3.21 min.

Using a similar procedure, the following compounds were prepared:

| Ex. No. | Structure | MW | LCMS M + 1 | $R_t$ |
|---|---|---|---|---|
| 5A | 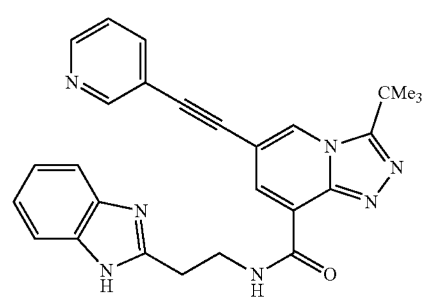 | 463 | 464 | 2.32 |

-continued

| Ex. No. | Structure | MW | LCMS M + 1 | $R_t$ |
|---|---|---|---|---|
| 5B | 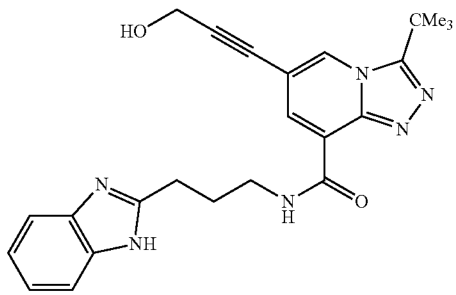 | 430 | 431 | 2.42 |

EXAMPLE 6

To a stirred solution of Example 5 (32 mg) in EtOH (3 mL) was added 10% Pd/C (20 mg) and the mixture was stirred under a hydrogen atmosphere for 15 h. The mixture was filtered and the filtrate was concentrated to leave a residue which was purified by column chromatography on silica gel (elution with 20:1 $CH_2Cl_2$:MeOH) to afford Example 6 (20 mg) as a light yellow solid. LCMS: M+1 is 497 at 2.91 min.

The following compound was prepared in the similar manner.

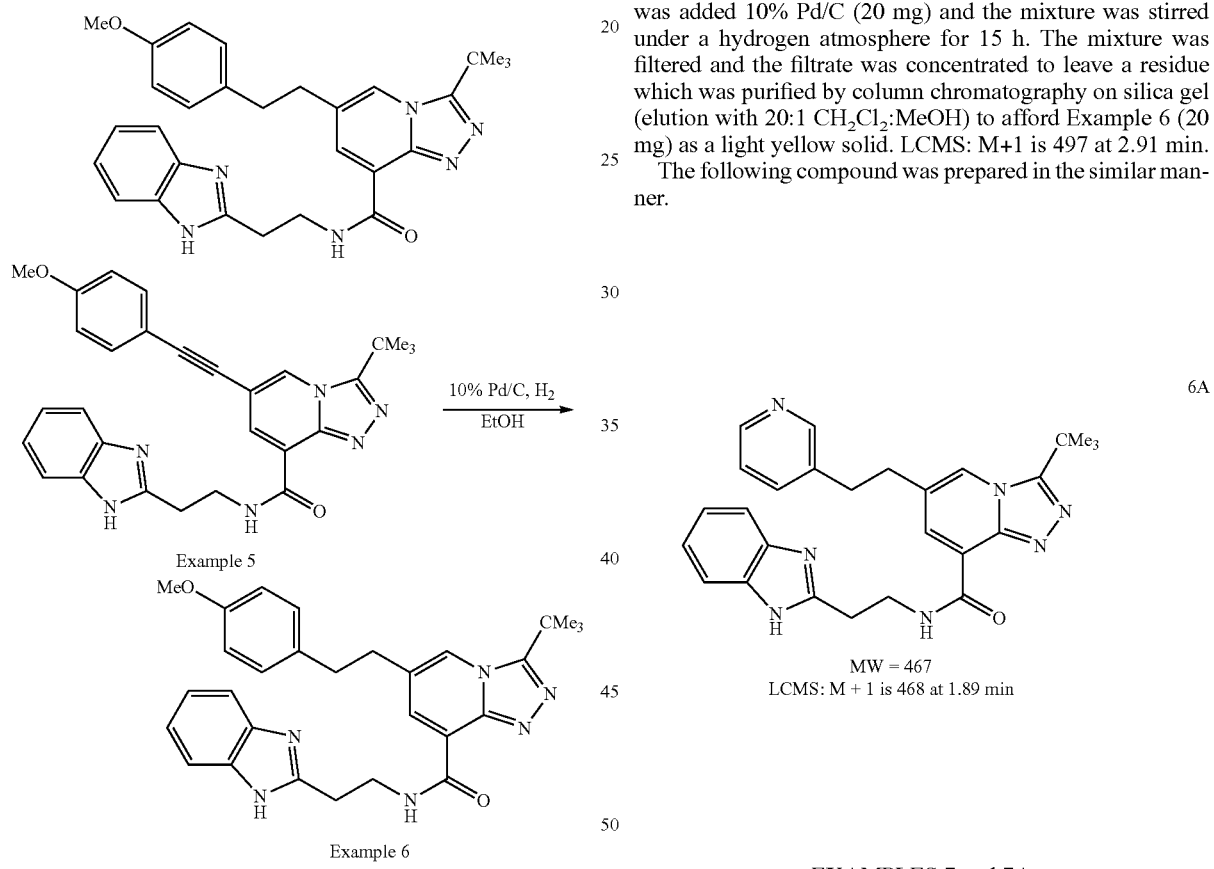

6A

MW = 467
LCMS: M + 1 is 468 at 1.89 min

EXAMPLES 7 and 7A

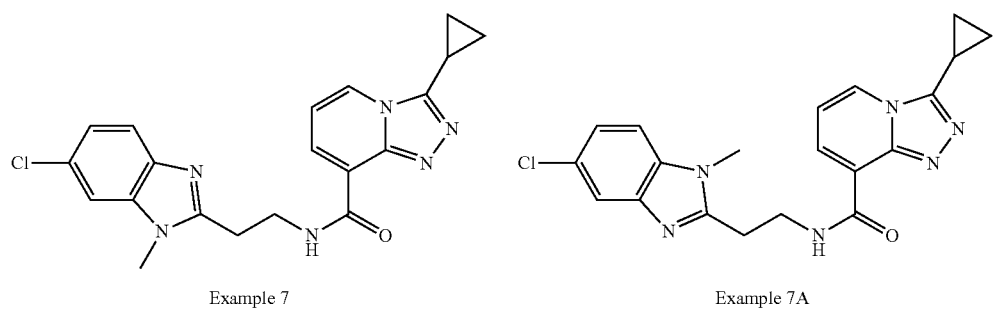

Example 7      Example 7A

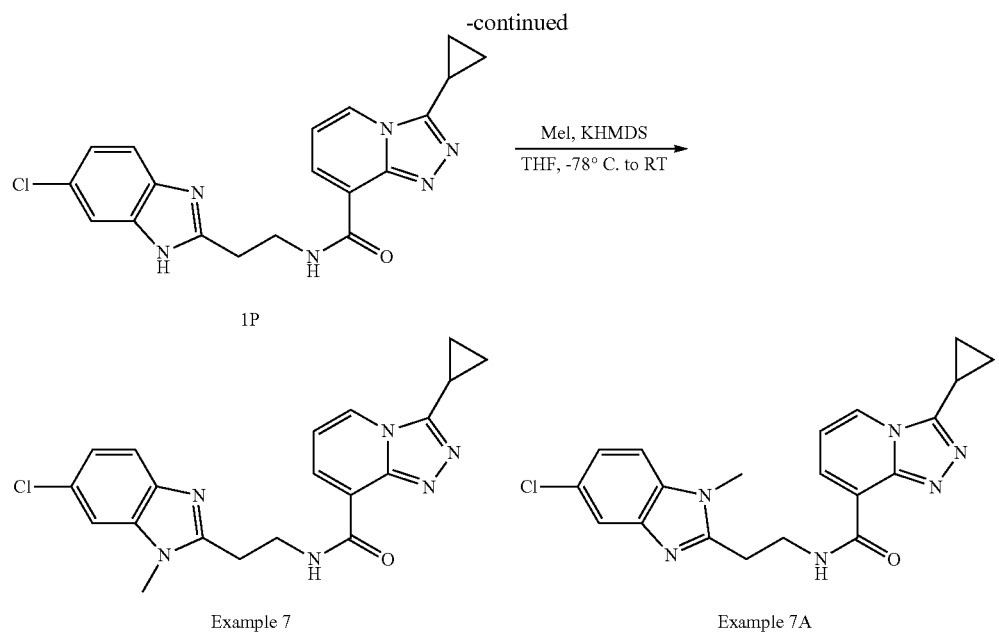

To a cold (−78° C.), stirred solution of 1P (104 mg) in anhydrous THF (8 mL) was added KHMDS (0.55 mL of 0.5 M solution in toluene). After being stirred at −78° C. for 30 min, MeI (0.019 mL) was added dropwise. The cold bath was removed and the mixture was warmed to RT and stirred overnight. The reaction was quenched with a saturated aqueous solution of $NaHCO_3$, extracted with EtOAc, dried over $MgSO_4$, and filtered. The filtrate was concentrated under vacuum to leave a residue which was purified by column chromatography on silica gel (elution with 0-20% acetone in $CH_2Cl_2$) to afford Example 7 (41 mg) and Example 7A (32 mg). LCMS: M+1 is 395 at 2.14 min (Example 7) and 395 at 2.10 min (Example 7A).

Using a similar procedure, the following compounds were prepared:

| Ex. No. | Structure | MW | LCMS M + 1 | $R_t$ |
|---|---|---|---|---|
| 7B | 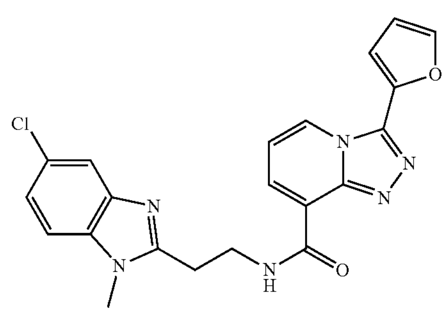 [SMILES: Cn1c(CCNC(=O)c2cccn3c(-c4ccco4)nnc23)nc2cc(Cl)ccc21] | 420 | 421 | 2.44 |
| 7C | 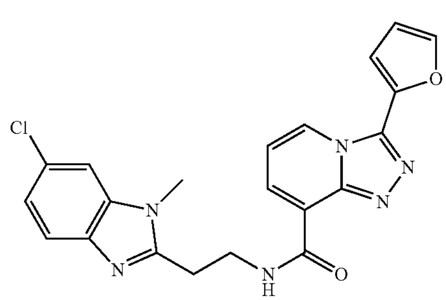 [SMILES: Cn1c(CCNC(=O)c2cccn3c(-c4ccco4)nnc23)nc2ccc(Cl)cc21] | 420 | 421 | 2.42 |

-continued

| Ex. No. | Structure | MW | LCMS M + 1 | R_t |
|---|---|---|---|---|
| 7D | 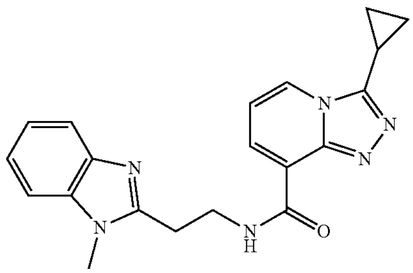 [SMILES: Cn1c(CCNC(=O)c2cccn3c(C4CC4)nnc23)nc2ccccc21] | 360 | 361 | 1.84 |
| 7E | 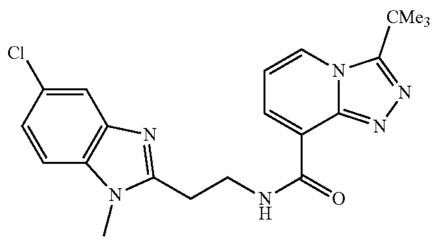 | 410 | 411 | 2.31 |
| 7F | 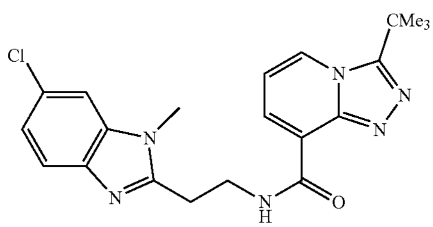 | 410 | 411 | 2.32 |
| 7G | 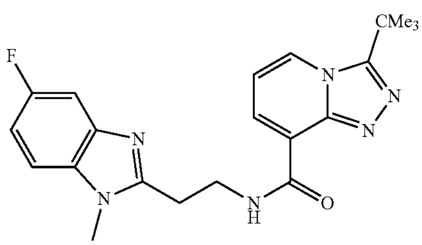 | 394 | 395 | 2.18 |
| 7H | 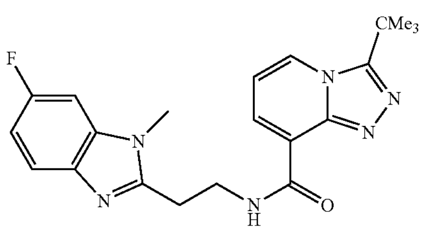 | 394 | 395 | 2.20 |
| 7I | 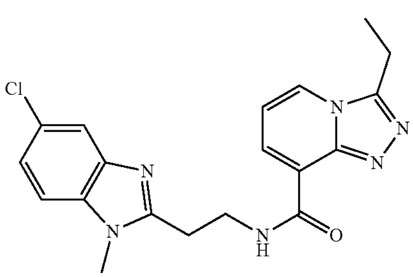 [SMILES: CCc1nnc2c(C(=O)NCCc3nc4cc(Cl)ccc4n3C)cccn12] | 382 | 383 | 1.98 |

-continued

| Ex. No. | Structure | MW | LCMS M + 1 | R$_t$ |
|---|---|---|---|---|
| 7J | 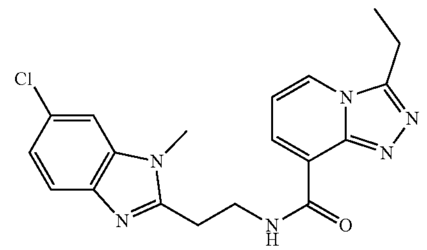 [SMILES: CCc1nnc2c(C(=O)NCCc3nc4ccc(Cl)cc4n3C)cccn12] | 382 | 383 | 2.02 |
| 7K | 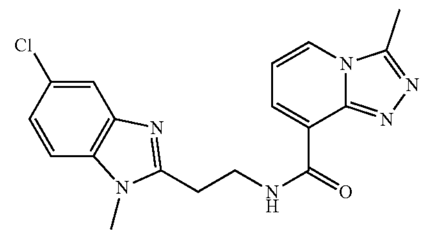 [SMILES: Cc1nnc2c(C(=O)NCCc3nc4cc(Cl)ccc4n3C)cccn12] | 368 | 369 | 1.85 |
| 7L | 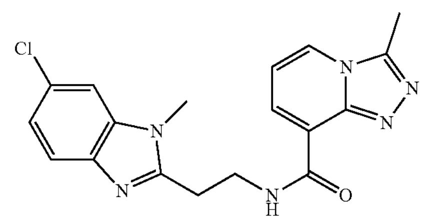 [SMILES: Cc1nnc2c(C(=O)NCCc3nc4ccc(Cl)cc4n3C)cccn12] | 368 | 369 | 1.87 |
| 7M | 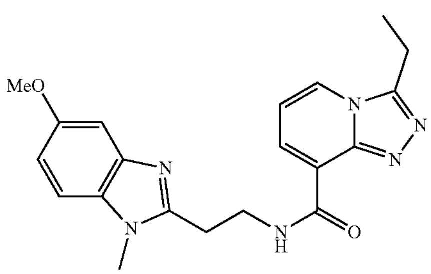 [SMILES: CCc1nnc2c(C(=O)NCCc3nc4cc(OC)ccc4n3C)cccn12] | 378 | 379 | 1.93 |
| 7N | 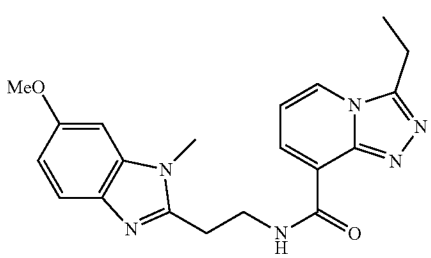 [SMILES: CCc1nnc2c(C(=O)NCCc3nc4ccc(OC)cc4n3C)cccn12] | 378 | 379 | 1.94 |
| 7O | 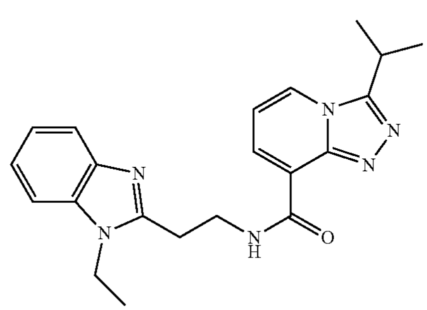 [SMILES: CCn1c(CCNC(=O)c2cccn3c(C(C)C)nnc23)nc2ccccc21] | 376 | 377 | 2.10 |

EXAMPLE 8

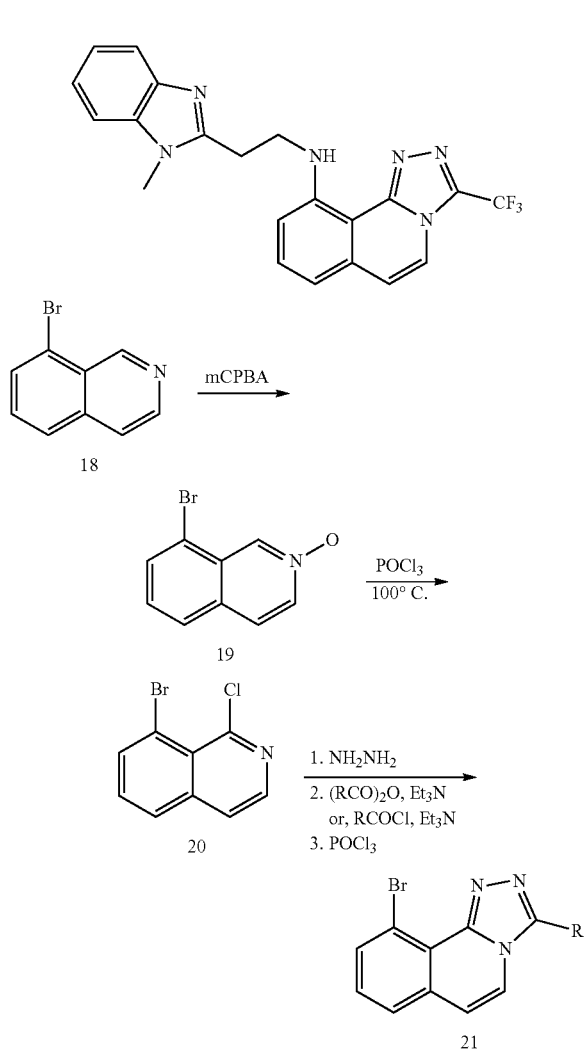

Step 1:

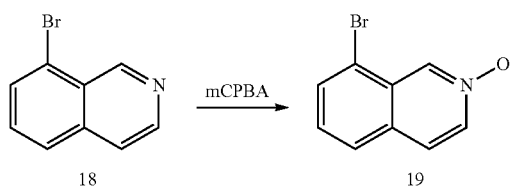

To a cold (0° C.), stirred solution of 18 (3.34 g) in CHCl$_3$ (35 mL) was added mCPBA (5.54 g of 77%) in one portion. The cold bath was removed and the mixture was stirred at RT for 3 h before being quenched with a saturated aqueous solution of Na$_2$CO$_3$. The organic layer was separated and the aqueous layer was extracted with CH$_2$Cl$_2$ (2×30 mL). The combined organic layers were dried over Mg$_2$SO$_4$, filtered, and concentrated under vacuum to yield N-oxide 19 which was directly used in the next step without further purification.

Step 2:

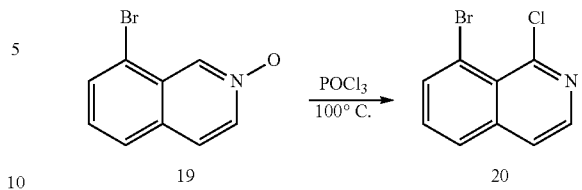

A solution of N-oxide 19 in POCl$_3$ (35 mL) was heated to 105° C. overnight, followed by heating at 120° C. for additional 20 h. The mixture was cooled to RT, poured into ice-water, and neutralized with NH$_4$OH solution. The resulting solution was extracted with CH$_2$Cl$_2$ (3×30 mL). The combined organic layers were dried over Mg$_2$SO$_4$, filtered, and concentrated under vacuum to leave a residue which was further purified by column chromatography on silica gel (elution with 10:1 hexane:ethyl acetate) to afford 20 (1.3 g) as a light brown solid. LCMS: M+2 is 244 at 4.45 min.

Step 3:

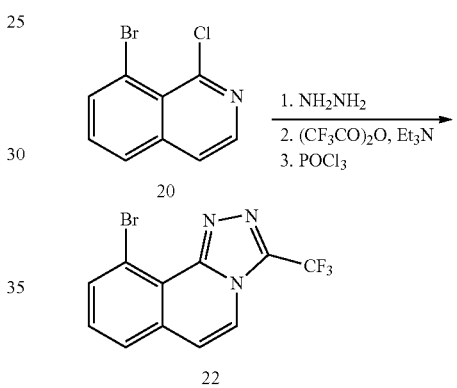

To a stirred solution of 20 (0.5 g) in 1,4-dioxane (20 mL) was added NH$_2$NH$_2$ (0.1 mL) and the mixture was heated to 64° C. overnight. Additional 0.1 mL of NH$_2$NH$_2$ was added and stirring was continued for additional 5 h at 64° C. Solvent was evaporated under vacuum and the residue was directly used in the next step without further purification.

To a cold (0° C.), stirred solution of product from above in anhydrous CH$_2$Cl$_2$ (6 mL) was added Et$_3$N (0.42 g) followed by trifluoroacetic anhydride (0.56 g) dropwise over 5 min via a syringe. After being stirred at 0° C. for 1 h and at RT for an additional 1 h, the reaction was quenched with H$_2$O (20 mL). The organic layer was separated and the aqueous layer was extracted with CH$_2$Cl$_2$ (3×20 mL). The combined organic layers were dried over Mg$_2$SO$_4$, filtered, and concentrated under vacuum to afford a solid which was used directly in the next step without further purification.

To a stirred solution of the intermediate from above in 1,2-dichloroethane (5 mL) was added POCl$_3$ (0.5 mL) and the mixture was heated at 84° C. overnight. The mixture was cooled to RT, poured into ice-water, and carefully neutralized with NH$_4$OH solution. The resulting solution was extracted with CH$_2$Cl$_2$ (3×20 mL). The combined organic layers were dried over Mg$_2$SO$_4$, filtered, and concentrated under vacuum to leave a residue which was purified by column chromatography on silica (elution with 50:1 CH$_2$Cl$_2$:MeOH) to afford 22 (0.31 g) as a light yellow solid. LCMS: M is 316 at 4.05 min.

The following compound was prepared in the similar fashion.

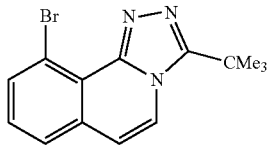

22-1

A mixture of bromide 22 (60 mg), amine 23 (60 mg), tris(dibenzylideneacetone)-dipalladium (0) (8.7 mg), BINAP (3.5 mg), and sodium tert-butoxide (55 mg) in toluene (1.5 mL) was heated to 115° C. in a sealed tube for 24 h. The reaction was cooled to RT and concentrated under vacuum to leave a residue which was purified by preparative TLC on silica gel (elution with 20:1 $CH_2Cl_2$:MeOH) to afford Example 8 (20 mg) as a solid. LCMS: M+1 is 411 at 3.27 min.

The following compounds were prepared in the similar manner.

| Ex. No. | Structure | MW | LCMS M + 1 | $R_t$ |
|---|---|---|---|---|
| 8A | 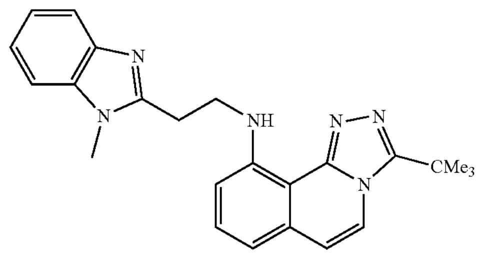 | 398 | 399 | 2.93 |
| 8B | 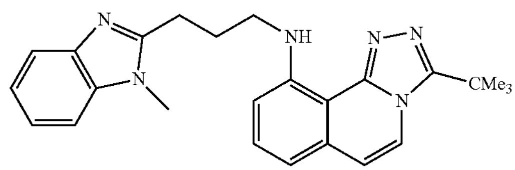 | 412 | 413 | 2.64 |
| 8C | 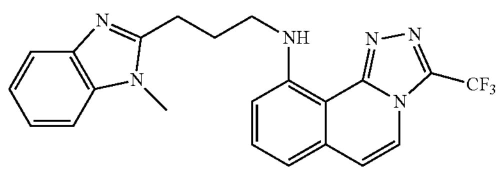 [SMILES: Cn1c(CCCNc2cccc3ccn4c(C(F)(F)F)nnc4c23)nc2ccccc21] | 424 | 425 | 3.18 |

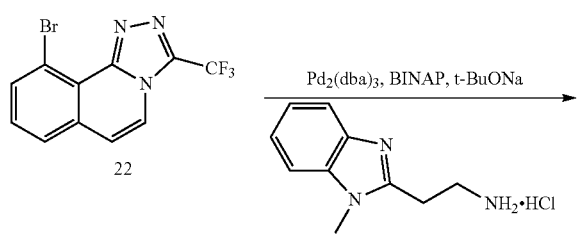

Step 4:

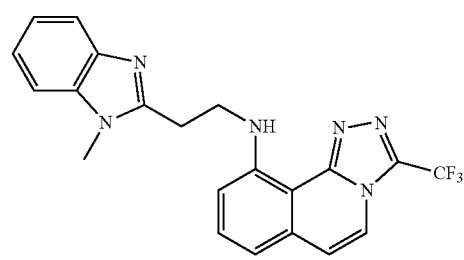

Example 8

The amount and frequency of administration of the active compound employed and/or the pharmaceutically acceptable salts thereof will be regulated according to the judgment of the attending clinician considering such factors as age, condition and size of the patient. A typical recommended dosage regimen can range from about 10 mg/dose to about 100 mg/dose, preferably about 10 to about 50 mg/dose, and more preferably about 20 to about 25 mg/dose.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy*, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

The activity of the compounds of Formula I and II can be determined by the following procedures.

In Vitro PDE10 Assay

PDE10A1 activity was measured in white opaque 384-well Opti-Plates (Perkin Elmer Life Sciences) using a scintillation proximity assay (GE Healthcare). Human recombinant PDE10A1 was purchased from BPS Bioscience, Inc. The reaction mixture contained PDE10A1 (0.02 nM), 10 nM [$^3$H] cAMP ([5',8-$^3$H]Adenosine 3',5'-cyclic phosphate, ammonium salt], Amersham) and various concentrations of compound in 50 mM Tris-HCl, pH 7.5, 8.3 mM MgCl$_2$, 17 mM EGTA and 0.2% bovine serum albumen in a total volume of 30 µl. The assay was initiated with the addition of substrate and was allowed to proceed for 30 minutes at room temperature before being stopped by the addition of 300 µg yttrium SPA PDE beads. The reaction mixtures were thoroughly mixed, and the beads were allowed to settle for 30 minutes. The plates were then counted in a TopCount scintillation counter. Under these conditions, less than 30% of the substrate was hydrolyzed in the absence of compound. Ki values were determined as described by Cheng and Prusoff (1973).

Using the test procedures described above, the following compounds of Formula I were found to have Ki values of less than 50 nM: Examples 1A, 1B, 1E, 1I, 1O, 1P, 1Q, 1R, 1S, 1T, 1AA, 1BB, 1DD, 1FF, 1GG, 1HH, 1II, 1LL, 1MM, 1NN, 1UU, 1XX, 1ZZ, 1BBB, 1DDD, 1FFF, 2B, 2D, 2F, 2G, 4A, 4D, 4E, 4F, 5B, 7A, 7D, 7E, 7K and 7O. The following compounds of Formula I were found to have Ki values of less than 10 nM: Examples 1GB, 1M, 1N, 1O, 1P, 1Q, 1Z, 1EE, 1SS, 1VV, 2B, 2F, 4D and 7O.

Using the test procedures described above, the following compounds of Formula II were found to have Ki values of less than 50 nM: Examples 8, 8B and 8C.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A compound of Formula I

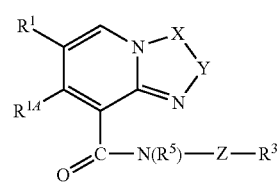

Formula I or a pharmaceutically acceptable salt thereof, wherein
—X—Y— is —N=C(R$^4$)—, —C(R$^4$)=N—;
R$^1$ is H, halo, alkyl, alkoxy, —CF$_3$, cycloalkyl, alkoxyalkyl, OH, hydroxyalkyl, —OCF$_3$, —O-cycloalkyl, benzyloxy, —C(O)Oalkyl, —O-alkyl-CO$_2$H, —C(O)N(R$^6$)$_2$, —N(R$^6$)$_2$, -alkylN(R$^6$)$_2$, —NR$^6$—C(O)N(R$^6$)$_2$, —N(R$^6$)C(O)Oalkyl, —N(R$^6$)SO$_2$-alkyl, CN, —SF$_5$, —OSF$_5$, —SO$_2$R$^6$, —SR$^6$, trimethylsilylphenyl, aryl, —C≡C—CH$_2$OH, —C≡C-aryl, arylalkyl-, —C(O)NHCH$_2$-aryl, heteroaryl, —C≡C-heteroaryl, heteroarylalkyl-, —C(O)NHCH$_2$-heteroaryl,

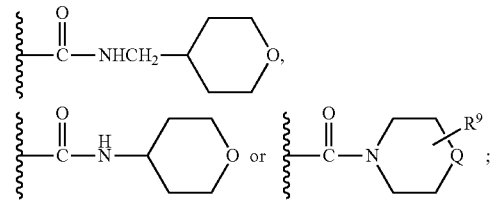

R$^{1A}$ is H, halo, alkyl, alkoxy, —CF$_3$, cycloalkyl, alkoxyalkyl, OH, hydroxyalkyl, —OCF$_3$, —O-cycloalkyl, benzyloxy, —C(O)Oalkyl, —O-alkyl-CO$_2$H, —C(O)N(R$^6$)$_2$, —N(R$^6$)$_2$, -alkylN(R$^6$)$_2$, —NR$^6$—C(O)N(R$^6$)$_2$, —N(R$^6$)C(O)Oalkyl, —N(R$^6$)SO$_2$-alkyl, CN, —SF$_5$, —OSF$_5$, —SO$_2$R$^6$, —SR$^6$, trimethylsilylphenyl, —C≡C—CH$_2$OH, —C≡C-aryl, or arylalkyl-;
Q is —O—, —N(R$^{10}$)—, —S—, —SO—, —SO$_2$— or —CH$_2$—;
Z is:
—(CH(R$^2$))$_n$—(CH(R$^{2A}$))$_m$—,

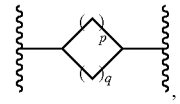

optionally substituted by 1 or 2 alkyl groups, or

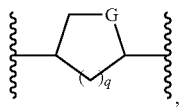

optionally substituted by 1 or 2 alkyl groups, wherein G is —N(R$^8$)—, —O— or —S—;
or —N(R$^5$)— and —Z— together form a 4 to 7 membered ring

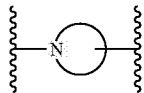

optionally substituted by 1 or 2 alkyl groups;
n is 1 or 2;
m is 0, 1 or 2;
p is 0, 1 or 2;
q is 0, 1, 2 or 3;
each R$^2$ is independently selected from the group consisting of H, alkyl or cycloalkyl;
each R$^{2A}$ is independently selected from the group consisting of H, alkyl, cycloalkyl, fluoro, OH, alkoxy, —N(R$^8$)$_2$ or -alkyl-N(R$^8$)$_2$;
R$^3$ is selected from the group consisting of pyridine, pyrazine,

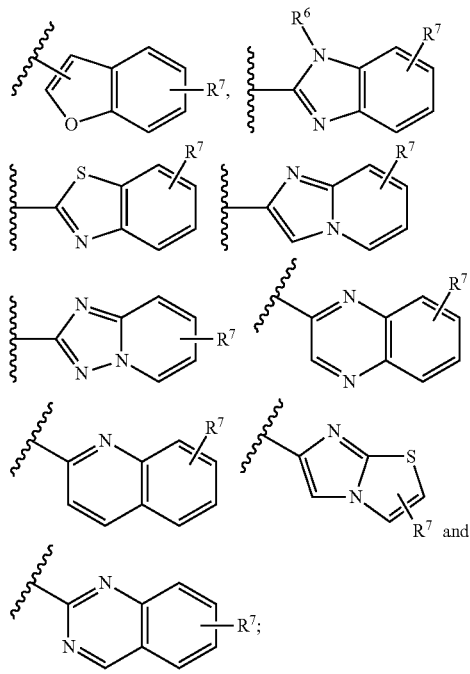

each R$^4$ is independently selected from the group consisting of H, alkyl, cycloalkyl, halo, —CF$_3$, alkoxyalkyl, heteroaryl, —CN, hydroxyalkyl, aryl, arylalkyl-, heteroarylalkyl-, —OCF$_3$, —SF$_5$, —OSF$_5$ and —N(R$^6$)$_2$;
R$^5$ is H, alkyl or cycloalkyl;
each R$^6$ is independently selected from the group consisting of H, alkyl, cycloalkyl and arylalkyl;

R$^7$ is 1 or 2 substituents independently selected from the group consisting of H, halo, alkyl, alkoxy, —CF$_3$, cycloalkyl, alkoxyalkoxy, OH, hydroxyalkyl, —OCF$_3$, —O-cycloalkyl, benzyloxy, —C(O)Oalkyl, —O-alkyl-CO$_2$H, —C(O)N(R$^6$)$_2$, —N(R$^6$)$_2$, -alkylN(R$^6$)$_2$, —NR$^6$—C(O)N(R$^6$)$_2$, —N(R$^6$)C(O)Oalkyl, —N(R$^6$)SO$_2$-alkyl, phenyl, CN, —SF$_5$, —OSF$_5$, —SO$_2$R$^6$, —SR$^6$ and trimethylsilyl;
each R$^8$ is independently selected from the group consisting of H and alkyl;
R$^9$ is 1 to 3 substituents independently selected from the group consisting of H and alkyl, and when Q is —CH$_2$—, R$^9$ can also be halo, OH, alkoxy or —CF$_3$; and
R$^{10}$ is H, alkyl, —C(O)N(R$^6$)$_2$, —C(O)Oalkyl, or —SO$_2$-alkyl.

2. The compound of claim 1 wherein:
—X—Y— is —C(R$^4$)=N— or —N=C(R$^4$)—;
Z is —(CH(R$^2$))$_n$—(CH(R$^{2A}$))$_m$—;
the sum of n and m is 1-3;
R$^2$ is H or alkyl;
R$^{2A}$ is H or alkyl;
R$^1$ is H, halo, pyridyl, optionally substituted phenyl or —C≡C—CH$_2$OH;
R$^3$ is

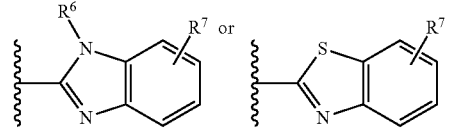

wherein R$^7$ is 1 or 2 substituents independently selected from H, halo, alkyl and alkoxy and R$^6$ is H or alkyl;
R$^4$ is alkyl, cycloalkyl, halo, —CF$_3$ or alkoxyalkyl; and
R$^5$ is H or alkyl
or a pharmaceutically acceptable salt thereof.

3. The compound of claim 2 wherein
—X—Y— is —C(R$^4$)=N— or —N=C(R$^4$)—;
Z is —(CH(R$^2$))$_n$—(CH(R$^{2A}$))$_m$—;
the sum of n and m is 1-3;
R$^2$ is H or alkyl;
R$^{2A}$ is H or alkyl;
R$^1$ is H, F, Br, pyridyl, OH-phenyl or —C≡C—CH$_2$OH;
R$^3$ is

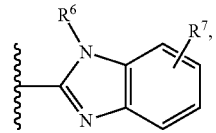

wherein R$^7$ is one substituent selected from the group consisting of H, F, Br, Cl and —OCH$_3$, or R$^7$ is two substituents independently selected from Cl and F, and wherein R$^6$ is H, methyl or ethyl;
R$^4$ is methyl, ethyl, propyl, isopropyl, t-butyl, cyclopropyl, cyclobutyl, Br, —CF$_3$ or methoxyethyl; and
R$^5$ is H or ethyl
or a pharmaceutically acceptable salt thereof.

4. The compound of claim 1 selected from the group consisting of Examples 1A, 1B, 1E, 1I, 1O, 1P, 1Q, 1R, 1S, 1T, 1AA, 1BB, 1DD, 1FF, 1GG, 1HH, 1II, 1LL, 1MM, 1NN, 1UU, 1XX, 1ZZ, 1BBB, 1DDD, 1FFF, 2B, 2D, 2F, 2G, 4A, 4D, 4E, 4F, 5B, 7A, 7D, 7E, 7K and 7O, or a pharmaceutically acceptable salt thereof.

5. A pharmaceutical composition, which comprises an effective amount of at least one compound of claim 1 or pharmaceutically acceptable salt thereof and a pharmaceutically acceptabale carrier.

* * * * *